United States Patent
Antoni et al.

(10) Patent No.: US 11,529,441 B2
(45) Date of Patent: *Dec. 20, 2022

(54) DRUG COMPOSITION AND COATING

(71) Applicant: W. L. Gore & Associates, Inc., Newark, DE (US)

(72) Inventors: Per Antoni, Upplands Väsby (SE); Karin Leontein, Upplands Väsby (SE); Mei Li, Flagstaff, AZ (US); Robert L. Cleek, Flagstaff, AZ (US); Paul D. Drumheller, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/733,588

(22) Filed: Jan. 3, 2020

(65) Prior Publication Data

US 2020/0139020 A1 May 7, 2020

Related U.S. Application Data

(63) Continuation of application No. 15/264,802, filed on Sep. 14, 2016, now Pat. No. 10,561,766.

(60) Provisional application No. 62/218,701, filed on Sep. 15, 2015.

(51) Int. Cl.
| | | |
|---|---|---|
| A61L 31/16 | (2006.01) | |
| A61L 31/08 | (2006.01) | |
| A61L 31/14 | (2006.01) | |
| A61L 27/54 | (2006.01) | |
| A61L 29/08 | (2006.01) | |
| A61L 27/28 | (2006.01) | |
| A61L 29/16 | (2006.01) | |

(52) U.S. Cl.
CPC ............... *A61L 31/16* (2013.01); *A61L 27/28* (2013.01); *A61L 27/54* (2013.01); *A61L 29/08* (2013.01); *A61L 29/16* (2013.01); *A61L 31/08* (2013.01); *A61L 31/148* (2013.01); *A61L 2300/416* (2013.01); *A61L 2300/606* (2013.01); *A61L 2300/802* (2013.01); *A61L 2420/02* (2013.01); *A61L 2420/06* (2013.01)

(58) Field of Classification Search
CPC .......... A61L 31/16; A61L 29/08; A61L 27/28; A61L 31/148; A61L 2300/802
See application file for complete search history.

(56) References Cited

U.S. PATENT DOCUMENTS

| | | |
|---|---|---|
| 3,953,566 A | 4/1976 | Gore |
| 4,187,390 A | 2/1980 | Gore |
| 5,876,432 A | 3/1999 | Lau et al. |
| 6,461,665 B1 | 10/2002 | Scholander |
| 6,743,388 B2 | 6/2004 | Sridharan et al. |
| 6,770,670 B2 | 8/2004 | Carver et al. |
| 7,049,380 B1 | 5/2006 | Chang et al. |
| 7,659,219 B2 | 2/2010 | Biran et al. |
| 8,048,440 B2 | 11/2011 | Chang et al. |
| 8,048,503 B2 | 11/2011 | Farnsworth et al. |
| 8,070,797 B2 | 12/2011 | Flanagan et al. |
| 8,658,707 B2 | 2/2014 | Xu et al. |
| 2003/0031715 A1* | 2/2003 | Park ................. A61K 47/32 514/651 |
| 2003/0204168 A1 | 10/2003 | Bosma et al. |
| 2004/0127551 A1 | 7/2004 | Zhang et al. |
| 2005/0055078 A1 | 3/2005 | Campbell |
| 2006/0067977 A1 | 3/2006 | Labrecque et al. |
| 2008/0118544 A1 | 5/2008 | Wang |
| 2008/0175980 A1 | 7/2008 | Sun |
| 2008/0255508 A1 | 10/2008 | Wang |
| 2009/0182413 A1 | 7/2009 | Burkart et al. |
| 2010/0015200 A1 | 1/2010 | Mcclain et al. |
| 2010/0209472 A1 | 8/2010 | Wang |
| 2010/0222311 A1 | 9/2010 | Thommes et al. |
| 2010/0233228 A1 | 9/2010 | Speck |
| 2010/0241220 A1 | 9/2010 | Mcclain et al. |
| 2010/0268321 A1 | 10/2010 | Mcdermott et al. |
| 2011/0144578 A1 | 6/2011 | Pacetti et al. |
| 2011/0295200 A1 | 12/2011 | Speck et al. |
| 2012/0172787 A1 | 7/2012 | Mcclain et al. |
| 2012/0277843 A1 | 11/2012 | Weber et al. |

(Continued)

FOREIGN PATENT DOCUMENTS

| | | |
|---|---|---|
| CN | 1096673 A | 12/1994 |
| CN | 101610798 A | 12/2009 |

(Continued)

OTHER PUBLICATIONS

Aggarwal et al. "Solid Dispersion as an Eminent Strategic Approach in Solubility Enhancement of Poorly Soluble Drugs" International Journal of Pharmaceutical Sciences and Research, 2010, 1 (8), pp. 1-13.

(Continued)

*Primary Examiner* — Andrew S Rosenthal

(57) ABSTRACT

According to the invention there is provided inter alia a medical device for delivering a paclitaxel to a tissue, the device the device having a coating layer applied to a surface of the device, the coating layer comprising components i), ii) and iii), wherein component i) is a therapeutic agent which is paclitaxel; and component ii) is urea or a pharmaceutically acceptable salt thereof, or a urea derivative or a pharmaceutically acceptable salt thereof; and component iii) is succinic acid, glutaric acid or caffeine, or a pharmaceutically acceptable salt of any one thereof.

17 Claims, 6 Drawing Sheets

(56) References Cited

U.S. PATENT DOCUMENTS

| | | |
|---|---|---|
| 2012/0310210 A1 | 12/2012 | Campbell et al. |
| 2013/0004548 A1 | 1/2013 | Klocke et al. |
| 2013/0142834 A1 | 6/2013 | Esfand et al. |
| 2013/0189329 A1 | 7/2013 | Wang |
| 2013/0231733 A1 | 9/2013 | Knisley et al. |
| 2013/0253426 A1 | 9/2013 | Campbell et al. |
| 2014/0135897 A1 | 5/2014 | Cully et al. |
| 2014/0142682 A1 | 5/2014 | Radspinner |
| 2016/0096006 A1 | 4/2016 | Cully et al. |
| 2017/0072116 A1 | 3/2017 | Antoni et al. |
| 2018/0104383 A1* | 4/2018 | Wang .............. A61L 29/08 |

FOREIGN PATENT DOCUMENTS

| | | |
|---|---|---|
| EP | 0086186 A1 | 8/1983 |
| EP | 0495820 B1 | 5/1995 |
| JP | 05-025045 A | 2/1993 |
| JP | 2002-201137 A | 7/2002 |
| JP | 2002-220340 A | 8/2002 |
| WO | 94/12198 A1 | 6/1994 |
| WO | 03/47508 A2 | 6/2003 |
| WO | 2004/000380 A1 | 12/2003 |
| WO | 2007/133699 A2 | 11/2007 |
| WO | 2008/063576 A2 | 5/2008 |
| WO | 2009/051614 A1 | 4/2009 |
| WO | 2009/064372 A2 | 5/2009 |
| WO | 2010/079218 A2 | 7/2010 |
| WO | 2011/110684 A1 | 9/2011 |
| WO | 2011/119159 A1 | 9/2011 |
| WO | 2011/147408 A2 | 12/2011 |
| WO | 2013/021199 A2 | 2/2013 |
| WO | 2013/074185 A1 | 5/2013 |
| WO | 2014/173748 A1 | 10/2014 |
| WO | 2015/136106 A1 | 9/2015 |
| WO | 2015/138862 A1 | 9/2015 |

OTHER PUBLICATIONS

Albers et al. "Evaluation of Predictive Models for Stable Solid Solution Formation" Journal of Pharmaceutical Sciences, 2011, 100(2), pp. 667-680.

Avula et al. "Predicting eutectic behaviour of drugs and excipients by unique calculations" J. Therm. Anal. Calorim. 2010, 99, pp. 655-658.

Avula et al. "Predicting Eutectic Behaviour of Drugs and Excipients by Unique Calculations" Proceedings of the NATAS Annual Conference on Thermal Analysis and Applications 2008, 36th.

Badjatya et al. "Enhancement of Solubility of Paclitaxel by Solid Dispersions Techniques" Asian Journal of Pharmacy & Life Science, 2011, 1(2), pp. 156-160.

Baird et al. "Evaluation and modeling of the eutectic composition of various drug-polyethylene glycol solid dispersions" Pharmaceutical Development and Technology, 2011, 16(3), pp. 201-211.

Brittain "Cocrystal Systems of Pharmaceutical Interest: 2009" Profiles of Drug Substances, Excipients, and Related Methodology, 2011, 36, pp. 361-381.

Camargo et al. "Injectable PLA-based in situ forming implants for controlled release of Ivermectin a BCS Class II drug: solvent selection based on physico-chemical characterization" Drug Development and Industrial Pharmacy, 2013, 39(1), pp. 146-155.

Chen et al. "Chiral co-crystal solid solution: structures, melting point phase diagram, and chiral enrichment of (ibuprofen)2(4,4-dipyridyl)" Cryst. Eng. Comm. 2010, 12, pp. 1485-1493.

Cherukuvada et al. "Eutectics as improved pharmaceutical materials: design, properties and characterization" Chem. Commun. 2014, 50, pp. 906-923.

Chiou et al. "Pharmaceutical Applications of Solid Dispersion Systems" Journal of Pharmaceutical Sciences, 1971, 60 (9), pp. 1281-1302.

Dake et al. "Polymer-free Paclitaxel-coated Zilver PTX Stents—Evaluation of Phamacokinetics and Comparative Safety in Porcine Arteries" Journal of Vascular and Interventional Radiology, 2011, 22, pp. 603-610.

Dinge "Eutectic mixtures of drugs with poor aqueous solubility. Solid state characterization and dissolution studies" Dissertation Abstracts International, 2012, 73 No. 9B(E).

Ekdahl et al. "Evaluation of the Blood Compatibility of Materials, Cells, and Tissues: Basic Concepts, Test Models, and Practical Guidelines" Advances in Experimental Medicine and Biology, 2013, Chapter 18, pp. 257-270.

Elder et al. "Use of pharmaceutical salts and cocrystals to address the issue of poor solubility" International Journal of Pharmaceutics, 2013, pp. 88-100.

Ford "The Current Status of Solid Dispersions" Pharm. Acta. Helv., 1986, 61(3), pp. 69-88.

Good et al. "Cocrystal Eutectic Constants and Prediction of Solubility Behavior" Crystal Growth and Design Communication 2010, 10, pp. 1028-1032.

Gordon et al. "Raman mapping of pharmaceuticals" International Journal of Pharmaceutics, 2011, 417, pp. 151-162.

Gorniak et al. "Phase Diagram and dissolution studies of the fenofibrate-acetylsalicylic acid system" J. Therm. Anal. Calorim. 2011, 104, pp. 1195-1200.

Gorniak et al. "Thermal, spectroscopic, and dissolution studies of the simvastatin-acetylsalicylic acid mixtures" J. Therm. Anal. Calorim. 2013, 111, pp. 2125-2132.

Goud et al. "Fast dissolving eutectic compositions of curcumin" International Journal of Pharmaceutics, 2012, pp. 63-72.

Gowthamarajan et al. "Dissolution Testing for Poorly Soluble Drugs: A Continuing Perspective" Dissolution Technologies, 2010, pp. 24-32.

Huuskonen et al. "Prediction of drug solubility from molecular structure using a drug-like training set" SAR and QSAR in Environmental Research, 2008, 19 (3-4), pp. 191-212.

Japanese Pharmaceutical Excipients Directory, p. 107-108 (no translation available).

Just et al. "Improved group contribution parameter set for the application of solubility parameters to melt extrusion" European Journal of Pharmaceutics and Biopharmaceutics, 2013, pp. 1-9.

Kitamoto et al. "Caffeine diminishes cytotoxic effects of paclitaxel on a human lung adenocarcinoma cell line" Cancer Letters, 2003, 191, pp. 101-107.

Kraitzer et al. "Mechanisms of antiproliferative drug release from bioresorable porous structures" Journal of Biomedical Materials Research A, 2013, 101A(5), pp. 1302-1310.

Kreuter "Solid Dispersion and Solid Solution" Topics in Pharmaceutical Sciences, 1983, pp. 359-370.

Lambert et al. "Radiation and Ethylene Oxide Terminal Sterilization Experiences with Drug Eluting Stent Products" AAPS PharmSciTech, 2011, 12(4), pp. 1116-1126.

Lappegard et al. "The artificial surface-induced whole blood inflammatory reaction revealed by increases in a series of chemokines and growth factors is largely complement dependent" Journal of Biomedical Materials Research Part A, 2008, 87A(1), pp. 129-135.

Larsen et al. "Assay of plasma heparin using thrombin and the chromogenic substrate H-D-Phe-Pip-Arg-pNA (S-2238)" Thrombosis Research, 1978, 13(2), pp. 285-288.

Lee et al. "Paclitaxel-coated expanded polytetrafluoroethylene haemodialysis grafts inhibit neointimal hyperplasia in porcine model of graft stenosis", Nephrology Dialysis Transplantation, 2006, 21, pp. 2432-2438.

Liao et al. "Vascular smooth cell proliferation in perfusion culture of porcine carotid arteries" Biochemical and Biophysical Research Communications, 2008, 372, pp. 668-673.

Liggins et al. "Solid-State Characterization of Paclitaxel" Journal of Pharmaceutical Sciences, 1997, 86(12), pp. 1458-1463.

Loh et al. "Paclitaxel Drug-Coated Balloons. A Review of Current Status and Emerging Applications in Native Coronary Artery De Novo Lesions" JACC: Cardiovascular Interventions, 2012, 5(10), pp. 1001-1012.

Lu et al. "A rapid thermal method for cocrystal screening" Cryst. Eng. Comm. 2008, 10, pp. 665-668.

Lu et al. "Controllable biodegradability, drug release behaviour and hemocompatibility of PTX-eluting magnesium stents" Colloids and Surfaces B: Biointerfaces, 2011, 83, pp. 23-28.

(56) References Cited

OTHER PUBLICATIONS

Lu et al. "Treatments of paclitaxel with poly(vinyl pyrrolidone) to improve drug release from poly(E-carprolactone) matrix for film-based stent" International Journal of Pharmaceutics, 2012, 434, pp. 161-168.

Luu et al. "High-throughput 96-well solvent mediated sonic blending synthesis and on-plate solid/solution stability characterization of pharmaceutical cocrystals" International Journal of Pharmaceutics, 2013, 441, pp. 356-364.

Meanwell "The Emerging Utility of Co-Crystals in Drug Discovery and Development" Annual Reports in Medicinal Chemistry, 2008, 43, pp. 373-404.

Moes et al. "Development of an oral solid dispersion formulation for use in low-dose metronomic chemotherapy of paclitaxel" European Journal of Pharmaceutics and Biopharmaceutics, 2013, 83, pp. 87-94.

Mohammad et al. "Hansen solubility parameter as a tool to predict cocrystal formulation" International Journal of Pharmaceutics, 2011, 407, pp. 63-71.

Muddukrishna et al. "Preparation and Solid State Characterization of Paclitaxel Cocrystals" Research J. Pharm. and Tech., 2014, 7(1), pp. 64-69.

Newa et al. "Preparation, characterization and in vivo evaluation of ibuprofen binary solid dispersions with poloxamer 188" International Journal of Pharmaceutics, 2007, 343, pp. 228-237.

Pasche et al. "Binding of Antithrombin to Immobilized Heparin Under Varying Flow Conditions" Artificial Organs, 1991, 15(6), pp. 481-491.

Scheinert et al. "The LEVANT I (Lutonix Paclitaxel-Coated Balloon for the Prevention of Femoropopliteal Restenosis) Trial for Femoropopliteal Revascularization" JACC: Cardiovascular Interventions, 2014, 7(1), pp. 10-19.

Scheller et al. "Paclitaxel Balloon Coating, a Novel Method for Prevention and Therapy of Restenosis" Journal of the American Heart Association, 2004, pp. 810-814.

Schierholz "Physico-chemical properties of a rifampicin-releasing polydimethyl-siloxane shunt" Biomaterials, 1997, 18, pp. 635-641.

Shen et al. "Enhanced Intestinal Absorption of Daidzein by Borneol/Menthol Eutectic Mixture and Microemulsion" AAPS PharmSciTech, 2011, 12(4), pp. 1044-1049.

Shen et al. "Incorporation of paclitaxel solid dispersions with poloxamer188 or polyethylene glycol to tune drug release from poly(E-carprolactone) films" Drug Development and Industrial Pharmacy, 2013, 39(8), pp. 1187-1196.

Simamora et al. "Emulsion Formulations for Intravenous Administration of Paclitaxel" PDA Journal of Pharmaceutical Science & Technology, 1998, 52(4), pp. 170-172.

Smith et al. "Quantitation of Glycosaminoglycan Hexosamine Using 3-Methyl-2-Benzothiazolone Hydrazone Hydrochloride" Analytical Biochemistry, 1979, 98(2), pp. 478-480.

Sohn et al. "Calorimetric investigation of the phase behaviour of the binary system 7-mPEG 5000-succinyloxy-methyloxycarbonyl-Paclitaxel (PP7)/water" e-Polymers, 2005, No. 007, pp. 1-9 (ISSN 1618-7229).

Stoebner et al. "Effect of processing methods on drug release profiles of anti-restenotic self-assembled monolayers" Applied Surface Science, 2012, 258, pp. 5061-5072.

Tajarobi et al. "Dissolution Rate Enhancement of Parabens in PEG Solid Dispersions and its Influence on the Release from Hydrophilic Matrix Tablets" Journal of Pharmaceutical Sciences, 2011, 100(1), pp. 275-283.

Tian et al. "Construction of Drug-Polymer Thermodynamic Phase Diagrams Using Flory-Huggins Interaction Theory: Identifying the Relevance of Temperature and Drug Weight Fraction to Phase Separation within Solid Dispersions" Mol. Pharmaceutics, 2013, 10, pp. 236-248.

Trask "An Overview of Pharmaceutical Cocrystals as Intellectual Property" Molecular Pharmaceutics, 2007, 4(3), pp. 301-309.

Vedantham et al. "Development of a probucol-releasing antithrombogenic drug eluting stent" Journal of Biomedical Materials Research B: Applied Biomaterials, 2012, 100B(4), pp. 1068-1077.

Vella-Zarb et al. "Small Molecule, Big Difference: The Role of Water in the Crystallization of Paclitaxel" Journal of Pharmaceutical Sciences, 2013, 102(2), pp. 674-683.

Vippagunta et al. "Factors Affecting the Formation of Eutectic Solid Dispersions and Their Dissolution Behaviour" Journal of Pharmaceutical Sciences, 2007, 96(2), pp. 294-304.

Yamashita et al. "Detection of Cocrystal Formation Based on Binary Phase Diagrams Using Thermal Analysis" Pharm Res., 2013, 30, pp. 70-80.

Yazdani et al. "Vascular, Downstream, and Pharmacokinetic Responses to Treatment with a Low Dose Drug-Coated Balloon in a Swine Femoral Artery Model" Catheterization and Cardiovascular Interventions, 2014, 83, pp. 132-140.

Yoon et al. "Establishment of a solvent map for formation of crystalline and amorphous paclitaxel by solvent evaporation process" Korean J. Chem. Eng., 2011, 28(9), pp. 1918-1923.

Yuan et al. "Influence of Physicochemical Properties on the In Vitro Skin Permeation of Enantiomers, Racemate, and Eutectics of Ibuprofen for Enhanced Transdermal Drug Delivery" Journal of Pharmaceutical Sciences, 2013, 102(6), pp. 1957-1969.

Zhang et al. "Crystalline and Amorphous Solids" Developing Solid Oral Dosage Forms: Pharmaceutical Theory and Practice; 2009, Chapter 2, pp. 25-60.

\* cited by examiner

DRUG COMPOSITION AND COATING

CROSS-REFERENCE TO RELATED APPLICATIONS

This application is a continuation of U.S. application Ser. No. 15/264,802, filed Sep. 14, 2016, which claims the benefit of U.S. Provisional Application No. 62/218,701, filed Sep. 15, 2015, both of which are herein incorporated by reference in their entireties.

FIELD OF THE INVENTION

The present invention relates to solid paclitaxel-containing compositions, medical devices with coatings comprising solid paclitaxel-containing compositions and to methods for making such compositions and coatings.

BACKGROUND OF THE INVENTION

It has become increasingly common to treat a variety of medical conditions by introducing a medical device into the vascular system within a human. For example, medical devices used for the treatment of vascular disease include stents, stent-grafts, grafts, catheters, balloon catheters, guide wires, cannulas and the like.

In the case of a localized vascular disease, a systemic administration of a drug may not be desirable because the drug may have unwanted effects on parts of the body which are not to be treated, or because treatment of the diseased vasculature requires a high concentration of drug that may not be achievable by systemic administration. It is therefore often desirable to administer drugs in a localized manner to vascular tissues. Several devices for localized drug delivery are known, including a stent coated with an elutable drug, also known as a drug eluting stent (DES), and a balloon catheter coated with an elutable drug, also known as a drug eluting balloon (DEB).

DEBs and DESs are coated with a drug using a variety of coating techniques. When a drug-eluting device is inserted into a vascular organ, the drug may be slowly released into the surrounding vascular tissue, to provide a long lasting therapeutic effect. Alternatively, the drug may be rapidly released from the coating, with minimal drug remaining on the device shortly after implantation. Coatings with fast drug release characteristics are particularly advantageous if a medical device is not permanently implanted, as it is necessary in this situation to rapidly deliver drug to the vascular tissue at the time of treatment.

Non-stent based local delivery systems, such as DEBs, have also been effective in the treatment of vascular disease. Therapy commences when the DEB is inserted into the patient to a target site, and inflated at the target site, wherein the DEB is pressed against the vascular tissue to deliver the drug. When DEBs are used, it is advantageous for the drug in the coating to be retained on the balloon surface prior to inflation, and to be rapidly released and transferred to the vascular tissue upon inflation.

One of the potential drawbacks to the use of drug-eluting devices for the localized treatment of vascular disease, is the unintended release of drug away from the target site. This unintended release may occur during removal from the packaging and insertion into the body, tracking to and placement at the treatment site, during expansion or deployment of the device, or occur post-treatment as the device is withdrawn from the body. Such unintended release may result from physical dislodgement of the coating, drug diffusion, device contact with areas proximate the treatment site, or washing out of the drug from the surface of the device due to blood flow.

A drug commonly used for the localized treatment of vascular disease is paclitaxel. Paclitaxel can be coated onto a medical device using a variety of coating techniques. One technique involves combining the paclitaxel with an excipient, either in dry form using powder methods, or in solution or in suspension using solvent methods. The paclitaxel-excipient combination is then applied to the surface of the medical device, either in the form of a powder or via the application of the solution or suspension followed by a drying step.

There are numerous factors that must be considered when creating a paclitaxel-excipient combination, and when coating the combination onto a medical device. In general, combining drugs and excipients, and coating medical devices with drug-excipient combinations, are complicated areas of technology. They involve the usual formulation challenges, such as those of oral or injectable pharmaceuticals, together with the added challenge of maintaining drug adherence to the medical device until it reaches the target site and subsequently delivering the drug to the target tissues with the desired release and absorption kinetics.

A commercially available paclitaxel-eluting device which is currently marketed under brand name IN.PACT Admiral Drug-Coated Balloon by Medtronic is a balloon with a coating which is a formulation comprising paclitaxel and urea.

US2011/0295200 (Speck et al.) describes catheter balloons covered with paclitaxel in hydrated crystalline form or in hydrated solvated crystalline form, which are said to have immediate release and bioavailability of a therapeutically effective amount of paclitaxel at the site of intervention. In one embodiment, the catheter balloon is coated by dissolving paclitaxel in an aqueous solvent in the presence of urea, then completely or partially wetting the balloon surface with the solution, then letting the solvent evaporate. It is noted that in the presence of urea in the coating layer of paclitaxel on the balloon surface, release of the drug from the surface was promoted.

There is a need to develop further paclitaxel-containing coatings for use in the localized treatment of vascular disease. In particular, there is a need to develop coatings for medical devices comprising paclitaxel that can deliver therapeutically relevant levels of paclitaxel to a target vascular tissue, in a localised manner, on a suitable timescale. The coating should have good adherence to the medical device during device preparation, manipulation and insertion, while also having suitable release characteristics once in contact with the target vascular tissue. The paclitaxel, when formulated in the coating, should be stable to sterilization, in particular ethylene oxide sterilization. When the medical device has a coating with an additional therapeutic agent (i.e. other than paclitaxel), the paclitaxel-containing coating should be compatible with the additional therapeutic agent.

SUMMARY OF THE INVENTION

The present inventors have prepared novel paclitaxel-excipient solid compositions which have been coated onto a variety of medical devices. The coated devices demonstrate suitable paclitaxel release characteristics when in contact with vascular tissue (as evidenced by in vitro and in vivo studies), while also exhibiting suitable adherence and durability. The paclitaxel present in the coating is also stable to sterilization, in particular ethylene oxide sterilization.

Furthermore, a paclitaxel-containing coating according to the invention coated onto a medical device already pre-coated with immobilized biologically active heparin (as an example of an additional therapeutic agent) was shown to retain therapeutically relevant levels of heparin bioactivity following removal of the outer paclitaxel-containing coating.

Thus, in one aspect, the invention provides a medical device for delivering a therapeutic agent to a tissue, the device having a coating layer applied to a surface of the device, the coating layer comprising components i), ii) and iii), wherein
component i) is a therapeutic agent which is paclitaxel; and
component ii) is urea or a pharmaceutically acceptable salt thereof, or a urea derivative or a pharmaceutically acceptable salt thereof; and
component iii) is succinic acid, glutaric acid or caffeine, or a pharmaceutically acceptable salt of any one thereof.

In another aspect, the invention provides a composition comprising a mixture of components i), ii) and iii), wherein
component i) is paclitaxel; and
component ii) is urea or a pharmaceutically acceptable salt thereof, or a urea derivative or a pharmaceutically acceptable salt thereof; and
component iii) is succinic acid, glutaric acid or caffeine, or a pharmaceutically acceptable salt of any one thereof.

DETAILED DESCRIPTION OF THE INVENTION

Figure 1:
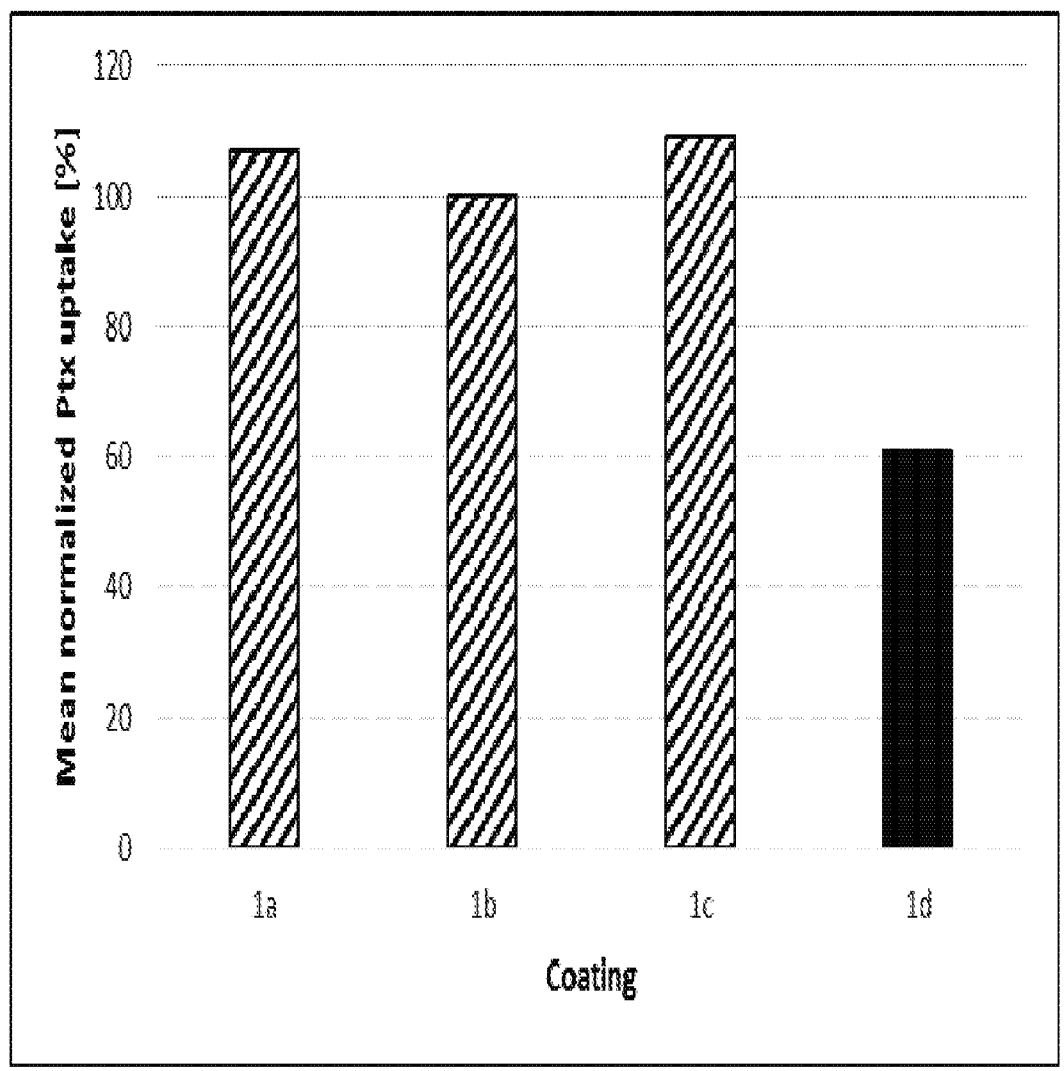
FIG. 1 shows the normalized percent uptake of paclitaxel (in vitro) in porcine tissue for coated stent-grafts of the invention compared with a comparator (Example 3).

The present invention relates to novel paclitaxel-containing solid compositions comprising components i), ii) and iii) as defined herein. Such compositions are particularly useful for coating medical devices.

Medical Devices and Materials

The medical devices of the present invention are suitable for a wide range of applications including, for example, a range of medical treatment applications within the body. Exemplary applications include use as a catheter balloon for transferring drug to, or placement of, or "touch-up" of implanted stents, stent-grafts or vascular grafts, use as stents, stent-grafts, catheters, a permanent or temporary prosthesis, or other type of medical implant, treating a targeted tissue within the body, and treating any body cavity, space, or hollow organ passage(s) such as blood vessels, the urinary tract, the intestinal tract, nasal or sinus cavities, neural sheaths, intervertebral regions, bone cavities, the oesophagus, intrauterine spaces, pancreatic and bile ducts, rectum, and those previously intervened body spaces that have implanted vascular grafts, stents, prosthesis, or other type of medical implants.

Additional examples of medical devices of the present invention include indwelling monitoring devices, artificial heart valves (leaflet, frame, and/or cuff), pacemaker or defibrillator electrodes, guidewires, cardiac leads, sutures, embolic filters, cardiopulmonary bypass circuits, cannulae, plugs, drug delivery devices, tissue patch devices, blood pumps, patches, osteoprostheses, chronic infusion lines, arterial lines, devices for continuous subarachnoid infusions, feeding tubes, CNS shunts (e.g., a ventriculopleural shunt, a ventriculo-atrial (VA) shunt, or a ventriculoperitoneal (VP) shunt), ventricular peritoneal shunts, ventricular atrial shunts, portosystemic shunts and shunts for ascites, devices for the filtering or removal of obstructions such as emboli and thrombi from blood vessels, as a dilation device to restore patency to an occluded body passage, as an occlusion device to selectively deliver a means to obstruct or fill a passage or space, and as a centering mechanism for transluminal instruments like catheters. In one embodiment, the medical devices of the present invention can be used to treat stent restenosis or treat tissue sites where previously placed drug-eluting constructs have failed. In another embodiment, medical devices as described herein can be used to establish, connect to, or maintain arteriovenous access sites, e.g., those used during kidney dialysis.

Further examples of medical devices of the present invention which can be permanent or temporary are catheters. Examples of catheters include, but are not limited to, central venous catheters, peripheral intravenous catheters, haemodialysis catheters, catheters such as coated catheters include implantable venous catheters, tunnelled venous catheters, coronary catheters useful for angiography, angioplasty, or ultrasound procedures in the heart or in peripheral veins and arteries, hepatic artery infusion catheters, CVC (central venous catheters), peripheral intravenous catheters, peripherally inserted central venous catheters (PIC lines), flow-directed balloon-tipped pulmonary artery catheters, total parenteral nutrition catheters, chronic dwelling catheters (e.g., chronic dwelling gastrointestinal catheters and chronic dwelling genitourinary catheters), peritoneal dialysis catheters, CPB catheters (cardiopulmonary bypass), urinary catheters and microcatheters (e.g. for intracranial application).

In one embodiment, the medical device is an expandable member. In another embodiment, the medical device is a balloon, a stent, a stent-graft or a graft.

Thus, in one embodiment, the medical device is an expandable member which, according to the present invention, can be a balloon, expandable catheter, stent, stent-graft, a self-expanding construct, a balloon expandable construct, a combination self-expanding and balloon expandable construct, a graft or a mechanical, radially expanding device which may be expanded, for example, via application of a torsional or longitudinal force. Expandable members can also include those which expand due to pneumatic or hydraulic pressure, those which expand due to magnetic forces, those which expand due to the application of energy (for example thermal, electrical, or ultrasonic (piezoelectric) energy). Expandable members can be placed temporarily in any lumen (e.g. a vessel) by expanding said device and then removed by collapsing said device by a torsional or longitudinal force.

In one embodiment, the medical device is a stent such as a bifurcated stent, balloon expandable stent or a self-expanding stent. Stents are configured as braids, wound wire forms, laser-cut forms, deposited materials, 3-D printed constructs, or combinations thereof, or take other structural forms, including those with length-adjustability, which provide support to a luminal wall or region. Stents are constructed of biocompatible materials including metals, metal alloys, such as stainless steel and nickel-titanium alloy (NiTi), polymers, ceramics, biodegradable materials (such as biodegradable polymers, ceramics, metals and metal alloys), or combinations thereof. Stents can be of substantially unitary form or comprise separate components, e.g., rings. Whether unitary or made up of components, stent structures can be joined together by struts, hinges, connectors, or materials which fully or partially line or cover the stent. In one embodiment, the stent structure is joined with fluoropolymers forming "webs" as described in US2009/0182413 (Gore Enterprise Holdings, Inc., incorporated herein by reference).

In one embodiment, the medical device is a stent such a bifurcated stent, a balloon expandable stent or a self-expanding stent. In one embodiment, the medical device is a stent formed from a metal, a metal alloy, a polymer, a ceramic, a biodegradable material, or a combination thereof.

In one embodiment, the medical device is a stent-graft. Stent-grafts combine at least one stent member with a graft component. Grafts are typically configured as tubular members, with closed walls or walls with openings. Graft materials include biocompatible materials such as fluoropolymers, including polytetrafluoroethylene (PTFE) and expanded polytetrafluoroethylene (ePTFE). Other suitable graft materials include polymers such as polyethylene terephthalate and ultra-high molecular weight polyethylene (UHMWPE). Graft materials can be made to possess different strengths, densities, dimensions, porosities and other functional characteristics and can take the form of films, extrusions, electrospun materials, coatings, depositions, or molded articles. Grafts may used alone or graft materials can fully or partially line or cover a stent structure. In one embodiment, the stent-graft can take forms as described in U.S. Pat. No. 5,876,432 (Gore Enterprise Holdings, Inc., incorporated herein by reference).

In one embodiment, the medical device is a stent graft, wherein the graft is formed from a polymer, suitably a biocompatible polymer. Suitably the graft is formed from a fluoropolymer such as expanded polytetrafluoroethylene (ePTFE). In one embodiment, the medical device is a graft.

Stents, stent-grafts and grafts can be overlain with various materials such as polymers and primer layers. In an embodiment, the stent or graft structure is modified to enhance the ability of the device to hold or release a therapeutic agent applied to the device. For example, pits or blind holes can be formed in stent struts into which a therapeutic agent is loaded. When coated onto a stent, stent-graft, or graft, the composition of the invention will release a therapeutic agent in a localized manner, therefore a stent, stent-graft or graft coated with a composition of the invention is referred to herein as a drug eluting stent (DES).

In one embodiment, the medical device is a medical balloon. Balloons useful in the invention may be formed by using any conventional manner such as extrusion, blow molding and other molding techniques. Balloons may be compliant or semi-compliant or non-compliant and may be of various lengths, diameters, sizes and shapes. Balloons can be so called "conformable" or "conforming", "length-adjustable" or "steerable" balloons. In other embodiments, the medical devices may comprise balloons which are constructed of wrapped films, are fiber-wound, are of variable length, are segmented, and/or have controlled or variable inflation profiles. In other embodiments, balloons may be overlain with a material or comprise more than one layer or be of composite construction. In an embodiment, the balloon surface or structure is modified to enhance the ability of the balloon to hold or release a therapeutic agent applied to it. For example, the balloon can be folded in such a way as to hold a therapeutic agent within said folds. When coated onto a balloon, the composition of the invention will release a therapeutic agent in a localized manner, therefore a balloon coated with a composition of the invention is referred to herein as a drug eluting balloon (DEB).

According to the invention the medical device, in particular a surface of the medical device, is composed of a synthetic or naturally occurring organic or inorganic polymer or material, including but not limited to materials such as polyolefins, polyesters, polyurethanes, polyamides, polyether block amides, polyimides, polycarbonates, polyphenylene sulfides, polyphenylene oxides, polyethers, silicones, polycarbonates, polyhydroxyethylmethacrylate, polyvinyl pyrrolidone, polyvinyl alcohol, rubber, silicone rubber, polyhydroxyacids, polyallylamine, polyallylalcohol, polyacrylamide, and polyacrylic acid, styrenic polymers, polytetrafluoroethylene and copolymers thereof, expanded polytetrafluoroethylene and copolymers thereof, derivatives thereof and mixtures thereof. Some of these classes are available both as thermosets and as thermoplastic polymers. As used herein, the term "copolymer" shall be used to refer to any polymer formed from two or more monomers, e.g. 2, 3, 4, 5 and so on and so forth. Bioresorbables, such as poly(D,L-lactide) and polyglycolids and copolymers thereof are also useful. Non-woven, bioabsorbable web materials comprising a tri-block copolymer such as poly(glycolide-co-trimethylene carbonate) tri-block copolymer (PGA: TMC) are also useful (as described in U.S. Pat. No. 7,659,219; Biran et al.). Useful polyamides include, but are not limited to, nylon 12, nylon 11, nylon 9, nylon 6/9 and nylon 6/6. Examples of some copolymers of such materials include the polyether-block-amides, available from Elf Atochem North America in Philadelphia, Pa. under the tradename of PEBAX®. Another suitable copolymer is a polyetheresteramide. Suitable polyester copolymers, include, for example, polyethylene terephthalate and polybutylene terephthalate, polyester ethers and polyester elastomer copolymers such as those available from DuPont in Wilmington, Del. under the tradename of HYTREL® Block copolymer elastomers such as those copolymers having styrene end blocks, and midblocks formed from butadiene, isoprene, ethylene/butylene, ethylene/propene, and so forth may be employed herein. Other styrenic block copolymers include acrylonitrile-styrene and acrylonitrile-butadiene-styrene block copolymers. Also, block copolymers wherein the particular block copolymer thermoplastic elastomers in which the block copolymer is made up of hard segments of a polyester or polyamide and soft segments of polyether may also be employed herein. Other useful materials are polystyrenes, poly(methyl) methacrylates, polyacrylonitriles, poly(vinylacetates), poly(vinyl alcohols), chlorine-containing polymers such as poly(vinyl) chloride, polyoxymethylenes, polycarbonates, polyamides, polyimides, polyurethanes, phenolics, aminoepoxy resins, polyesters, silicones, cellulose-based plastics, and rubber-like plastics. Combinations of these materials can be employed with and without cross-linking. Polymeric materials may optionally be blended with fillers and/or colorants, such as a gold, barium, or tantalum filler to render the polymeric material radiopaque. Polymeric materials may optionally be modified at their surface while retaining bulk properties using methods known in the art, such as acid or base etching, hydrolysis, aminolysis, plasma modification, plasma grafting, corona discharge modification, chemical vapour deposition, ion implantation, ion sputtering, ozonation, photomodification, electron beam modification, gamma beam modification, and the like.

In an embodiment, a surface of the medical device is composed of nylon.

In one embodiment, the medical device, in particular a surface of the medical device is biocompatible and comprises or consists of a polyether-block-amides, such as PEBAX®.

The medical device, in particular a surface of the medical device, may be composed of one or more fluorinated polymers such as fluoropolymers, e.g. expanded polytetrafluoroethylene (ePTFE), polytetrafluoroethylene (PTFE), fluorinated ethylene-propylene (FEP), perfluorocarbon copolymers, e.g. tetrafluoroethylene perfluoroalkylvinyl ether (TFE/PAVE) copolymers, copolymers of tetrafluoroethylene (TFE) and perfluoromethyl vinyl ether (PMVE), copolymers of TFE with functional monomers that comprise acetate, alcohol, amine, amide, sulfonate, functional groups and the like as described in U.S. Pat. No. 8,658,707 (W. L. Gore and Associates, incorporated herein by reference, as well as combinations thereof. Also contemplated are combinations of the above with and without crosslinking between the polymer chains, expanded polyethylene, polyvinylchloride, polyurethane, silicone, polyethylene, polypropylene, polyurethane, polyglycolic acid, polyesters, polyamides, elastomers and their mixtures, blends and copolymers or derivatives thereof. ePTFE has a porous microstructure which is particularly compatible with the coating of the invention. Suitably a surface of the medical device is composed of ePTFE.

As used herein, the term "porous" refer to a material having openings, for example spaces (or pores) between ePTFE nodes and fibrils. Usually, as in the case of ePTFE, the pores of a porous material contain air when the material is not "wetted". The porosity of a device composed of ePTFE can be evaluated using various methods and parameters, as described in US2013/0231733 (W.L. Gore & Associates, Inc., incorporated herein by reference).

The medical device, in particular a surface of the medical device, may also be composed of one or more metals, including, but are not limited to, biocompatible metals, titanium, stainless steel, high nitrogen stainless steel, gold, silver, rhodium, zinc, platinum, rubidium, copper and magnesium, and combinations thereof. Suitable alloys include cobalt alloys including cobalt-chromium alloys such as L-605, MP35N, Elgiloy, titanium alloys including nickel-titanium alloys (such as Nitinol), tantalum, and niobium alloys, such as Nb-1% Zr, and others. In one embodiment, the medical device is a stent and is composed of biocompatible metal selected from stainless steel, tantalum, titanium alloys and cobalt alloys. The medical device, in particular a surface of the medical device may also be composed of a ceramic substrate including, but are not limited to, silicone oxides, aluminum oxides, alumina, silica, hydroxyapatites, glasses, calcium oxides, polysilanols, and phosphorous oxide.

In one embodiment, the medical device is covered with a porous material onto which a coating layer of the present invention is applied. In one embodiment, at least a portion of the surface of the device being coated is porous. In an embodiment, the medical device covering material is a fluoropolymer such as polytetrafluoroethylene (PTFE) or an expanded PTFE (ePTFE). The structure of expanded PTFE characterized by nodes interconnected by fibrils, is taught in U.S. Pat. Nos. 3,953,566 and 4,187,390 (W. L. Gore & Associates; both incorporated herein by reference). In one embodiment, the fluoropolymer medical device covering comprises ePTFE having a material structure with fibrils or fibrils and nodes. In another embodiment, the fibrils or fibrils and nodes change in size, dimension, or orientation as a dimension of the expandable member covering is changed. In one embodiment, the medical device is a balloon, disposed over at least a part of which is a covering, the covering being made at least in part of ePTFE, and disposed over at least a portion of the ePTFE balloon covering is a coating of the present invention.

In one embodiment, the medical device comprises a covering disposed around at least a portion of a coating layer of the invention. Such a covering may also be described as a sheath. In one embodiment the covering is removable from over the coating layer. In one embodiment, the covering is disposed over a coating layer of the invention applied to an expandable member. The covering can comprise any biocompatible material, including any possessing porosity or permeability. In one embodiment, the porosity or permeability varies as the material is deformed or otherwise altered in dimension.

Materials which may exhibit porosities or permeabilities that change with changes in the dimension of covering include, but are not limited to, fibrillated structures, such as expanded fluoropolymers (for example, expanded polytetrafluoroethylene (ePTFE)) or expanded polyethylene (as described in U.S. Pat. No. 6,743,388 (Sridharan et al.) and incorporated herein by reference); fibrous structures (such as woven or braided fabrics; non-woven mats of fibers, microfibers, or nanofibers; materials made from processes such as electrospinning or flash spinning; polymer materials consisting of melt or solution processable materials such as fluoropolymers, polyamides, polyurethanes, polyolefins, polyesters, polyglycolic acid (PGA), polylactic acid (PLA), and trimethylene carbonate (TMC), and the like; films with openings created during processing (such as laser- or mechanically-drilled holes); open cell foams; microporous membranes made from materials such as fluoropolymers, polyamides, polyurethanes, polyolefins, polyesters, PGA, PLA, TMC, and the like; porous polyglycolide-co-trimethylene carbonate (PGA:TMC) materials (as described in U.S. Pat. No. 8,048,503 (Gore Enterprise Holdings, Inc.)) and incorporated herein by reference); or combinations of the above. Processing of the above materials may be used to modulate, enhance or control porosity or permeability between a first, closed state and second, more porous or permeable state. Such processing may help close the material structure (thus lowering porosity or permeability) in a first state, help open the material structure in a second state, or a combination of both. Such processing which may help close the material structure may include, but is not limited to: calendaring, coating (discontinuously or continuously), compaction, densification, coalescing, thermal cycling, or retraction and the like. Such processing that may help open the material structure may include, but is not limited to: expansion, perforation, slitting, patterned densification and/or coating, and the like. In another embodiment, said materials comprise pores between fibrils or between nodes interconnected by fibrils, such as in ePTFE.

One skilled in the art will appreciate various methods which characterize the change in porosity or permeability using testing at a first state comparing to testing done at a second state. These methods include, but are not limited to, characterizations of air or liquid flux across the material structure at a given pressure differential, characterization which determines the pressure differential at which different fluids strike through the material structure such as Water Entry Pressure or Bubble Point, and visual characterization as measured from an image (e.g. from a scanning electron microscope or light microscope).

In one embodiment, the covering material is a fluoropolymer such as expanded polytetrafluoroethylene (ePTFE), polytetrafluoroethylene (PTFE), fluorinated ethylene-propylene (FEP), perfluorocarbon copolymers, e.g. tetrafluoroethylene perfluoroalkylvinyl ether (TFE/PAVE) copolymers, copolymers of tetrafluoroethylene (TFE) and perfluoromethyl vinyl ether (PMVE), or copolymers of TFE with functional monomers that comprise acetate, alcohol, amine, amide, sulfonate, functional groups and the like as described in U.S. Pat. No. 8,658,707 (W. L. Gore and Associates, incorporated herein by reference), as well as combinations thereof.

In another embodiment, the fluoropolymer covering possesses a material structure which changes as a dimension of the covering changes. In one embodiment, the fluoropolymer covering comprises ePTFE having a material structure with fibrils or fibrils and nodes. In another embodiment, the fibrils or fibrils and nodes change in size, dimension, or orientation as a dimension of the covering is changed. In one embodiment, the medical device is a balloon, disposed over at least a part of which is a covering, the covering being made at least in part of ePTFE, and the material structure of the ePTFE changes upon expansion of the balloon.

In another embodiment, the medical device is a balloon, disposed over at least a part of which is a coating layer of the invention which in turn is covered at least in part with a covering such as a sheath, the covering being made at least in part of ePTFE, and the material structure of the ePTFE changes upon expansion of the balloon. In one embodiment, the porosity or permeability of the covering is sufficiently low so as to prevent substantial movement of material in the coating layer from moving through the covering. In another embodiment, the porosity or permeability of the covering increases upon expansion of the balloon and allows at least some of the material in the coating layer to transfer from the surface of the balloon. In one embodiment, the transferred material is a paclitaxel-excipient solid composition of the invention. Once the paclitaxel-excipient solid composition passes through the outer covering, it is delivered to a treatment site.

In one embodiment the covering is essentially hydrophobic and is treated to render it hydrophilic using, for example, the methods described in US2013/0253426 (W. L. Gore & Associates; incorporated herein by reference). In another embodiment, the covering comprises a film or film tube of ePTFE.

In another embodiment of the invention, the surface(s) or outward configuration of the covering material may be modified with textures, protrusions, wires, blades, spikes, scorers, depressions, grooves, coatings, particles, and the like. In another embodiment of the invention, the surface(s) or outward configuration of the covering material may be modified with needles, cannulae, and the like. These modifications may serve various purposes such as to modify tissues into which therapeutic agents will be (or have been) delivered, control placement of the system of the invention, and direct fluid transfer. Such textures may help in increased transfer of a therapeutic agent onto, more deeply and/or into deeper tissues. Such textures may be comprised of the covering material, or may be comprised of an added material.

In another embodiment of the invention, the location(s) of the permeable microstructure may be varied. For example, a covering may be constructed such that only a portion of its microstructure is variably permeable. Such a configuration may be desirable where fluid transfer is not desired to occur, for example, at one or both of the ends of the expandable medical device of the invention. This may be desirable where multiple drug eluting devices will be used in a specific anatomy, and it would be undesirable to overlap treatments sites, i.e., delivering too much drug to a particular site.

In another embodiment, the covering may contain or be marked with radiopaque markers or be constructed to be radiopaque in its entirety. Such radiopaque indicators are used by clinicians to properly track and place an expandable medical device of the invention.

The solid composition of the invention comprising components i), ii) and iii), can be applied to the entire surface of the medical device, or only a portion of the surface of the medical device. Certain devices may have an external surface and an internal surface, either or both of which can be coated. For example, tubular substrates including but not limited to artificial blood vessels, vascular grafts, stents, and stent grafts, have an internal surface, or lumen, which can be coated independently from the external surface. A device comprising an internal and an external surface may only require the external surface to be coated. Conversely, only the internal surface may require a coating of the invention. In one embodiment, the amount or thickness of the coating may be varied over the surface of the medical device. The coating layer can be continuous over an entire surface of the device or be discontinuous and cover only a portion or separate portions of the device. The coating layer can also be "sculpted" or modified to create a desired surface topography or modified with textures, as described supra.

In one embodiment, up to 99%, for example up to 95%, 90%, 75%, 50% or 25% of the surface area of the medical device is coated with the coating of the invention. In one embodiment, both the external and internal surfaces of the medical device are coated. In another embodiment, only the external surface of the medical device is coated.

Composition and Coating Layer

The paclitaxel-containing solid compositions of the invention comprising components i), ii) and iii) are of use in coating medical devices. In the context of being used as a coating in a layer on a medical device, the paclitaxel-containing solid compositions are therefore referred to herein as being "coatings of the invention" or "the coating layers of the invention". Coatings of the invention are solid. For the avoidance of doubt, statements below made with respect to the coating of the invention will also apply (if appropriate) to the composition of the invention, unless otherwise stated.

Figure 6:
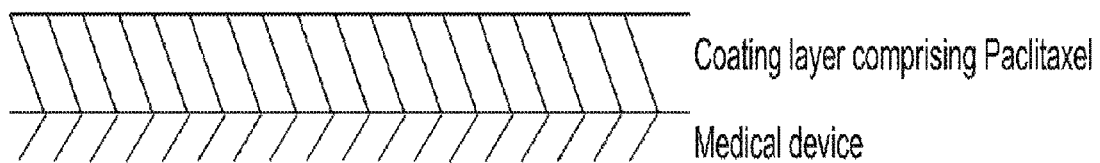
FIG. 6 is a schematic drawing of a coating layer according to the invention applied to a medical device.

A non-limiting embodiment of the invention is illustrated in FIG. 6.

The paclitaxel-containing solid composition and coating layer comprise a therapeutic agent which is paclitaxel (component i)); urea or a derivative thereof (component ii)); and succinic acid, glutaric acid or caffeine (component iii)).

Component i)

Paclitaxel is sold commercially in formulations for the treatment of various cancers and for the prevention and treatment of restenosis. Paclitaxel is known to exist in several different physical forms, including amorphous and crystalline forms, wherein the crystalline forms can be further differentiated into a number of different polymorphs. Furthermore, crystalline paclitaxel can exist as an anhydrate or in hydrated form. Reference to paclitaxel is also intended to include isotopically enriched derivatives of paclitaxel (for example paclitaxel wherein one or more hydrogen atoms is replaced with deuterium ($^2$H), or one or more carbon atoms is carbon-13 ($^{13}$C)) and pharmaceutically acceptable salts of paclitaxel. The accepted melting point of crystalline paclitaxel is circa 220° C., depending on the heating conditions and polymorph form (Liggins et al. "Solid-state characterization of paclitaxel", J. Pharm. Sci. 1997, Vol. 86, pages 1458-1463). It is known that the particular form of paclitaxel can affect the physical properties of the drug when in solid form. In particular, the adherence of paclitaxel to a surface may be influenced by its physical form, as can its rate of dissolution from a surface to the surroundings. Thus, formulating paclitaxel for solid delivery can be challenging at the first instance, and the effect of formulating paclitaxel in solid form with an excipient cannot easily be predicted.

As mentioned above, paclitaxel can have an optional amount of coordinated solvent, e.g. can be present in the composition in the form of a solvate, such as a hydrate. A hydrate of paclitaxel may have 2, 3 or 4 molecules of water, or in cases where paclitaxel dimers are formed, may have a non-integer number of molecule of water associated with each paclitaxel molecule. In one embodiment, the paclitaxel is anhydrous paclitaxel. In another embodiment, the paclitaxel is in the form of a paclitaxel hydrate such as paclitaxel dihydrate (i.e. 2 molecules of water). Paclitaxel dihydrate may be formed in situ by crystallisation of paclitaxel from solution in acetone/water when the coating is applied to the medical device as a solution. In an alternative embodiment, both anhydrous and hydrated forms of paclitaxel are present.

Component ii)

The composition and coating of the invention also comprise urea or a pharmaceutically acceptable salt thereof, or a urea derivative or a pharmaceutically acceptable salt thereof.

Urea has the Chemical Formula:

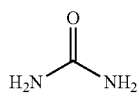

which may also be represented as $CO(NH_2)_2$.

Derivatives of urea include compounds with "N(CO)N" functionality e.g. $R_2N(CO)NR_2$ (wherein R represents a substituent), $RHN(CO)NR_2$, $RHN(CO)NHR$, $H_2N(CO)NR_2$, and $H_2N(CO)NHR$, and pharmaceutically acceptable salts thereof.

In one embodiment, component ii) is of formula (I):

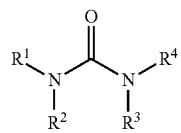

wherein,
$R^1$, $R^2$, $R^3$ and $R^4$ are independently H or $C_{1-15}$ alkyl optionally substituted by one or more (e.g. one) —OH groups, such as $C_{1-10}$ alkyl, $C_{1-8}$ alkyl or $C_{1-4}$ alkyl each optionally substituted by one or more (e.g. one) —OH groups;
or $R^2$ and $R^3$ together with the —N($R^1$)C(=O)N($R^4$)— moiety form a 5-7 membered ring optionally substituted by —OH, or a pharmaceutically acceptable salt thereof.

In one embodiment, component ii) is of formula (I):

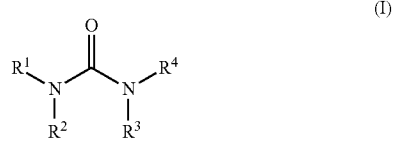

wherein,
$R^1$, $R^2$, $R^3$ and $R^4$ are independently H or $C_{1-15}$ alkyl, such as $C_{1-10}$ alkyl, $C_{1-8}$ alkyl or $C_{1-4}$ alkyl;
or $R^2$ and $R^3$ together with the —N($R^1$)C(=O)N($R^4$)— moiety form a 5-7 membered ring, or a pharmaceutically acceptable salt thereof. For example, $R^2$ and $R^3$ may be joined and represent $(CH_2)_2$ or $(CH_2)_3$.

In one embodiment, component ii) is of formula (I) and is not in form of a pharmaceutically acceptable salt. In a further embodiment, $R^1$ and $R^2$ are H. In a further embodiment, $R^3$ and $R^4$ are not H. In a still further embodiment, $R^1$, $R^2$ and $R^3$ are H.

In one embodiment, component ii) is methylurea, ethylurea, propylurea, butylurea, pentylurea, or octylurea. In one embodiment, component ii) is (2-hydroxyethyl)urea. Suitably, component ii) is ethylurea. In another embodiment, component ii) is urea.

Component iii)

The composition and coating of the invention also comprise a single excipient selected from succinic acid, glutaric acid and caffeine, or a pharmaceutically acceptable salt of any one thereof.

Succinic Acid has the Following Structure:

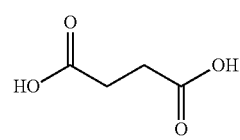

In one embodiment, component iii) is succinic acid or a pharmaceutically acceptable salt thereof. Suitably component iii) is succinic acid (i.e. not in the form of a pharmaceutically acceptable salt).

Glutaric Acid has the Following Structure:

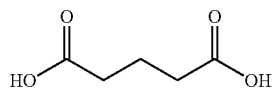

In one embodiment, component iii) is glutaric acid or a pharmaceutically acceptable salt thereof. Suitably component iii) is glutaric acid (i.e. not in the form of a pharmaceutically acceptable salt).

Exemplary pharmaceutically acceptable salts of succinic acid and glutaric acid include salts formed with Group 1 and Group 2 metals—such as sodium, potassium, magnesium and calcium, as well as inorganic salts such as ammonium salts.

Caffeine has the following structure:

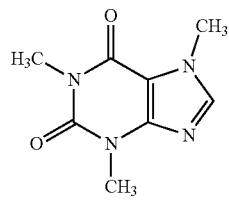

In one embodiment, component iii) is caffeine or a pharmaceutically acceptable salt thereof. Suitably component iii) is caffeine (i.e. not in the form of a pharmaceutically acceptable salt).

Exemplary pharmaceutically acceptable salts of caffeine include acid addition salts formed with inorganic and organic acids—such as HCl, HBr, acetic acid, methane sulfonic acid and benzene sulfonic acid.

In one embodiment, the composition and coating layer do not contain any polymeric components. The term "non-polymeric" will be clear to a person of skill in the art as meaning a substance which does not contain multiple repeating monomer units. Typically, a polymer will consist of at least 5 repeating monomer units, for example at least 6, at least 7, at least 8 or at least 9 repeating monomer units. References to polymers are intended to include copolymers. Examples of polymeric substances include proteins, poly (lactic-co-glycolic) acid (PLGA), polyvinylpyrrolidone (PVP), polyethylene glycol (PEG), poloxamers and shellac.

In one embodiment, the composition and coating layer are plasticizer-free i.e. does not contain a plasticizer. Plasticizers are defined herein as compounds that increase the plasticity or fluidity of a material, usually a polymer. Plasticizers can be in monomeric, oligomeric or polymeric form. Examples of plasticizers include acetic acid, formic acid, 1-butanol, 2-butanol, ethanol, 2-methyl-1-butanol, 2-methyl-1-propanol, 1-pentanol, 1-propanol, 2-propanol, ethyl acetate, ethyl formate, isopropyl acetate, methyl acetate, propyl acetate, anisole, tert-butylmethyl ether, ethyl ether, cumene, heptane, pentane, acetone, methylethyl ketone, methylisobutyl ketone, dimethyl sulfoxide, glycerin, polyethylene glycols, polyethylene glycol monomethyl ether, sorbitol, sorbitan, citrate esters including acetyl tributyl citrate, acetyl triethyl citrate, tributyl citrate, triethyl citrate and the like, castor oil, diacetylated monoglycerides, dibutyl sebacate, diethyl phthalate, triacetin, fractionated coconut oil, and acetylated monoglycerides.

The paclitaxel, when formulated in the composition and coating layer, should be able to withstand a sterilization process essentially intact. Thus, in one embodiment, component i) when formulated in the coating layer, is stable to sterilization, in particular ethylene oxide sterilization. Paclitaxel within the composition and coating layer is defined as being essentially intact after sterilization, or is considered to be stable to sterilization, if it exhibits no more than 20% degradation after sterilization without aging, for example no more than 15%, 10%, 9%, 8%, 7%, 6%, 5%, 4%, 3%, 2% or 1% degradation. The paclitaxel is considered to be degraded if it is chemically altered following sterilization. Conversely, paclitaxel in the composition and coating layer is defined as being essentially intact after sterilization, or is considered to be stable to sterilization, if the composition and coating retains at least 80% w/w of the paclitaxel chemical content after sterilization, for example at least 85%, 90%, 91%, 92%, 93%, 94%, 95%, 96%, 97%, 98%, 99% w/w or substantially all of the paclitaxel chemical content after sterilization.

The amount of intact paclitaxel in the composition and coating following sterilization can be determined using high-performance liquid chromatography (HPLC) techniques such as ultra-performance liquid chromatography (UPLC), for example using the UPLC method described in the Evaluation methods section.

Suitable sterilization processes include, but are not limited to sterilization using ethylene oxide, vapour hydrogen peroxide, plasma phase hydrogen peroxide, dry heat, autoclave steam sterilization, chlorine dioxide sterilization, gamma ray sterilization or electron beam sterilization. In one embodiment, the paclitaxel is essentially intact after ethylene oxide sterilization, vapour hydrogen peroxide sterilization, plasma phase hydrogen peroxide sterilization or electron beam sterilization. In one embodiment, the paclitaxel is stable to ethylene oxide sterilization, vapour hydrogen peroxide sterilization, plasma phase hydrogen peroxide sterilization or electron beam sterilization (or indeed multiple sterilization methods). Sterilization using ethylene oxide is the most commonly utilized, proven and readily available sterilization technique for implantable medical devices such as stents, stent grafts, balloons and balloon catheters. Thus, in one embodiment, the paclitaxel is essentially intact after sterilization using ethylene oxide. In another embodiment, the paclitaxel is stable to ethylene oxide sterilization.

Specific evaluation methods "Test Method E", "Test Method F", "Test Method G", and "Test Method H" are provided in the Test Methods section for assessing stability to sterilization using ethylene oxide, electron beam, vapour hydrogen peroxide, and plasma hydrogen peroxide, respectively.

As described in Example 13, coated balloons of the invention were sterilized using ethylene oxide (Test Method E) and then analysed for the presence of known paclitaxel degradation products using UPLC. All coated balloons tested were found to contain less than 1% of degradation products indicating that the paclitaxel within the coating was stable to sterilization by ethylene oxide.

Thus, in one aspect of the invention is provided a coated medical device as described herein which has been sterilized, e.g. ethylene oxide sterilized. In another aspect of the invention is provided a composition as described herein which has been sterilized, e.g. ethylene oxide sterilized.

In one embodiment, at least 80%, such as at least 85%, 90% or 95% by weight of paclitaxel (component i) is retained following sterilization using Test Method E.

The composition and coating layer suitably do not contain conventional surfactants. Conventional surfactants are defined herein as compounds that are amphiphilic and contain both hydrophobic and hydrophilic groups and include ionic, non-ionic, zwitterionic, aliphatic and aromatic surfactants. Surfactants can be in monomeric, oligomeric or polymeric form. Examples of surfactants include, but are not limited to, polysorbate (Tween® 20, Tween® 40, Tween® 60), PEG-fatty esters, PEG mega-3 fatty esters, PEG ethers (such as Triton X-100/octoxynol-9) and alcohols (such as tyloxapol), glycerol fatty esters, sorbitan fatty esters, PEG, glyceryl fatty esters, PEG sorbitan fatty esters, PEG sugar esters, poloxamers (which may be sold under the trade names of Synperonics®, Pluronics® and Kolliphor®), ascorbyl palmitate and p-isononylphenoxypolyglycidol (Olin 10-G® or Surfactant 10-G®).

In one embodiment, the composition and coating of the invention are free of cyclodextrin.

In one embodiment, the composition and coating of the invention are free of inorganic components (e.g. salts having both inorganic cations and inorganic anions). Suitably the coating of the invention is bioabsorbable or is biostable.

In one embodiment, the composition and coating layer consist of components i), ii) and iii). In this embodiment, the composition and coating layer do not comprise components other than paclitaxel, urea or a derivative thereof and one of succinic acid, glutaric acid and caffeine.

The relative amounts of components i), ii) and iii) can be varied to provide a coating with the desired properties. Such variation is well within the ordinary skill set of a skilled person preparing a coating for a medical device. In one embodiment, the proportion of component i) in the composition and coating layer is 10-95% by weight, such as 40-90%, 50-90%, 60-90%, 70-90% or 75-85% by weight based on the total weight of solid components added. In one embodiment, the proportion of component ii) in the composition and coating layer is 1-95% by weight, such as 5-80%, 5-50%, 5-30%, 5-20% or 5-15% by weight based on the total weight of solid components added. In one embodiment, the proportion of component iii) in the composition and coating layer is 1-95% by weight, such as 5-80%, 5-50%, 5-30%, 5-20% or 5-15% by weight based on the total weight of solid components added.

Suitably, the coating layer comprises a mixture of components i), ii) and iii) i.e. components i), ii) and iii) are present in a single coating layer. As will be discussed below, such a coating layer is suitably obtained by evaporation of a solution of components i), ii) and iii) in a solvent applied to a surface of the medical device.

The coating layer of the invention need not be applied directly to a surface of the medical device. Embodiments of medical devices coated with a composition of the invention can also include additional coatings underlying or overlaying the composition of the invention. Such additional coatings are separate and distinct from the coating layer of the invention. Such additional coatings can be used to increase adherence between the device surfaces and the composition of the invention or used to limit or meter elution of therapeutic agents from the composition. These additional coatings can include other therapeutic agents (such as those listed below), alone or in combination with various excipients or carriers. In one embodiment, the amount or thickness of the additional coating may be varied over the surface of the medical device. The additional coating layer can be continuous over an entire surface of the device or be discontinuous and cover only a portion or separate portions of the device. The additional coating layer can also be "sculpted" or modified to create a desired surface topography or texture.

In one embodiment, an adherent layer is interposed between the coating layer of the invention and the material of the surface of the device. The adherent layer, which is a separate and distinct layer underlying the paclitaxel-containing coating layer (coating layer comprising components i), ii) and iii)) improves the adherence of the drug coating layer to the surface of the medical device and further maintains the integrity of the coating, particularly during transit to the tissue to the be treated. In one embodiment, the adherent layer comprises a polymer, which is suitably biocompatible and avoids irritation of body tissue. Examples of such polymers include, but are not limited to polyolefins, polyisobutylene, ethylene-α-olefin copolymers, acrylic polymers and copolymers, polyvinyl chloride, polyvinyl methyl ether, polyvinylidene fluoride and polyvinylidene chloride, fluoropolymers, e.g. expanded polytetrafluoroethylene (ePTFE), polytetrafluoroethylene (PTFE), fluorinated ethylene-propylene (FEP), perfluorocarbon copolymers, e.g. tetrafluoroethylene perfluoroalkylvinyl ether (TFE/PAVE) copolymers, copolymers of tetrafluoroethylene (TFE) and perfluoromethyl vinyl ether (PMVE), copolymers of TFE with functional monomers that comprise acetate, alcohol, amine, amide, sulfonate, functional groups and the like as described in U.S. Pat. No. 8,658,707 (W. L. Gore and Associates, incorporated herein by reference, as well as combinations thereof), polyacrylonitrile, polyvinyl ketones, polystyrene, polyvinyl acetate, ethylene-methyl methacrylate copolymers, acrylonitrile-styrene copolymers, ABS resins, Nylon 12 and its block copolymers, polycaprolactone, polyoxymethylenes, polyethers, epoxy resins, polyurethanes, rayon-triacetate, cellulose, cellulose acetate, cellulose butyrate, cellophane, cellulose nitrate, cellulose propionate, cellulose ethers, carboxymethyl cellulose, chitins, polylactic acid, polyglycolic acid, polylactic acid-polyethylene oxide copolymers, polyethylene glycol, polypropylene glycol, polyvinyl alcohol, elastomeric polymers such as silicones (e.g., polysiloxanes and substituted polysiloxanes), polyurethanes, thermoplastic elastomers, ethylene vinyl acetate copolymers, polyolefin elastomers, EPDM rubbers and mixtures thereof.

Figure 7:
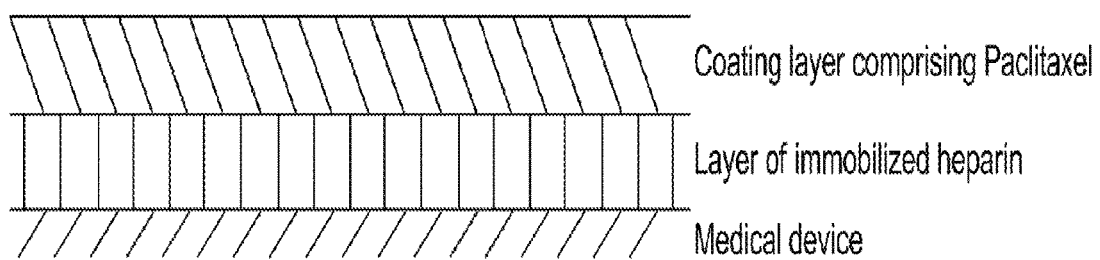
FIG. 7 is a schematic drawing of a coating layer according to the invention applied to a medical device, said device being also provided with a coating layer of immobilized heparin.

In another embodiment, an additional coating layer comprising a therapeutic agent other than paclitaxel is interposed between the coating layer of the invention and the material of the surface of the device. Said coating layer is a separate and distinct layer underlying the paclitaxel-containing coating layer (comprising components i), ii) and iii)) and may provide a therapeutic benefit in addition to the benefit provided by the paclitaxel i.e. allowing for adjunctive therapies to be combined with the paclitaxel-organic additive. For example, a coating of the invention can be applied to a medical device already coated with a biologically active immobilized heparin coating, while maintaining the activity of both coatings (i.e. the anti-proliferative effect of the paclitaxel-organic additive composition and the antithrombin III (ATIII) binding activity of the heparin, as measured by known analytical methods. A non-limiting embodiment of this aspect of the invention is illustrated in FIG. 7. Thus, coated medical devices of the invention with a heparin bonded under-coating appear to have the added benefit of producing a reduction in thrombosis after implantation.

Various methods for preparing a coating of immobilized heparin on a medical device are presented in Example 14. Suitable methods for assessing the heparin bioactivity of a medical device include those described in Test Methods L and M.

Example 1 describes such an embodiment, in which stent-grafts pre-coated with a layer of immobilized heparin were further coated with a paclitaxel-containing composition of the invention (components i), ii) and iii)). As shown in Example 15, when the paclitaxel-containing coating was removed from the surface of the stent-graft, the underlying immobilized heparin surface retained a therapeutically relevant level of heparin bioactivity.

Thus, in one embodiment, the additional coating layer comprises a therapeutic agent other than paclitaxel. Alternatively, said additional coating layer comprising a therapeutic agent other than paclitaxel will overlay a portion, or all of the coating layer of the invention. As described above, such coating layer is a separate and distinct layer overlying the paclitaxel-organic additive(s) coating layer.

In one embodiment, the additional coating layer comprises a therapeutic agent selected from cilostazol, everolimus, dicumarol, zotarolimus, carvedilol, anti-thrombotic agents such as heparin, heparin derivatives, urokinase, and dextrophenylalanine proline arginine chloromethylketone; antiinflammatory agents such as dexamethasone, prednisolone, corticosterone, budesonide, estrogen, sulfasalazine and mesalamine, sirolimus and everolimus (and related analogs), anti-neoplastic/antiproliferative/anti-miotic agents such as major taxane domain-binding drugs, such as paclitaxel and analogues thereof, epothilone, discodermolide, docetaxel, paclitaxel protein-bound particles such as ABRAXANE® (ABRAXANE is a registered trademark of ABRAXIS BIO-SCIENCE, LLC), paclitaxel complexed with an appropriate cyclodextrin (or cyclodextrin like molecule), rapamycin and analogues thereof, rapamycin (or rapamycin analogs) complexed with an appropriate cyclodextrin (or cyclodextrin like molecule), 17β-estradiol, 17β-estradiol complexed with an appropriate cyclodextrin, dicumarol, dicumarol complexed with an appropriate cyclodextrin, β-lapachone and analogues thereof, 5-fluorouracil, cisplatin, vinblastine, cladribine, vincristine, epothilones, endostatin, angiostatin, angiopeptin, monoclonal antibodies capable of blocking smooth muscle cell proliferation, and thymidine kinase inhibitors; lytic agents; anaesthetic agents such as lidocaine, bupivacaine and ropivacaine; anti-coagulants such as D-Phe-Pro-Arg chloromethyl ketone, an RGD peptide-containing compound, AZX100 a cell peptide that mimics HSP20 (Capstone Therapeutics Corp., USA), heparin, hirudin, antithrombin compounds, platelet receptor antagonists, antithrombin antibodies, anti-platelet receptor antibodies, aspirin, prostaglandin inhibitors, platelet inhibitors and tick antiplatelet peptides; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, Afunctional molecules consisting of a growth factor and a cytotoxin, b (functional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; agents that interfere with endogenous vasoactive mechanisms; inhibitors of leukocyte recruitment, such as monoclonal antibodies; cytokines; hormones, radiopaque agents such as iodinated contrast agents, gold, or barium, or a combination thereof. Suitably an additional coating layer comprises heparin.

Thus, in one embodiment, the medical device of the invention additionally comprises a coating layer of immobilized heparin, particularly a coating layer of immobilized heparin to which the paclitaxel containing coating layer is applied. Non-limiting methods for preparing an immobilized heparin coating on a medical device are described in Example 14.

In one embodiment, the medical device further comprises a protective top coat overlying the surface of the coating layer of the invention. The top coat may further minimise loss of the paclitaxel-containing layer before it is brought into contact with target tissues, for example during device assembly and packaging, transit to the site to be treated, or if the device is a balloon, stent, stent-graft or graft, during the first moments of inflation or expansion before coating layer is pressed into direct contact with target tissue. The top coat may be of particular use during crush loading, for example when an expandable medical device such as a balloon, stent, stent-graft or graft is coated in its expanded form, before being contracted into its non-expanded form. The contracted form of the coated device will usually be stored for a period of time before use. A top coating may prevent loss of the coating layer of the invention during storage and during expansion when the device is deployed. Alternatively, or additionally, the top coat may have lubricious properties to reduce frictional forces on the device while in transit. Suitably the top coat is degradable or soluble and will release slowly in the body lumen while protecting the drug layer. The top layer will erode more slowly if it is comprised of more hydrophobic, high molecular weight additives. Surfactants are examples of more hydrophobic structures with long fatty chains, such as Tween 20 and polyglyceryl oleate. High molecular weight additives include polyethylene oxide, polyethylene glycol, and polyvinyl pyrrolidone. Hydrophobic drug itself can act as a top layer component. For example, paclitaxel or rapamycin are hydrophobic. They can be used in the top layer. On the other hand, the top layer cannot erode too slowly or it might actually slow the release of drug during deployment at the target site. Other additives useful in the top coat include additives that strongly interact with drug or with the coating layer, such as p-isononylphenoxypolyglycidol, PEG laurate, Tween 20, Tween 40, Tween 60, PEG oleate, PEG stearate, PEG glyceryl laurate, PEG glyceryl oleate, PEG glyceryl stearate, polyglyceryl laurate, polyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-[beta]-D-glucopyranoside, n-decyl-[beta]-D-maltopyranoside, n-dodecyl-[beta]-D-glucopyranoside, n-dodecyl-[beta]-D-maltoside, heptanoyl-N-methylglucamide, n-heptyl-[beta]-D-glucopyranoside, n-heptyl-[beta]-D-thioglucoside, n-hexyl-[beta]-D-glucopyranoside, nonanoyl-N-methylglucamide, n-noyl-[beta]-D-glucopyranoside, octanoyl-N-methylglucamide, n-octyl-[beta]-D-glucopyranoside, octyl-[beta]-D-thioglucopyranoside; cysteine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, fibrinogens, lipases, benzalkonium chloride, benzethonium chloride, docecyl trimethyl ammonium bromide, sodium docecylsulfates, dialkyl methylbenzyl ammonium chloride, and dialkylesters of sodium sulfosuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol), and penta(propylene glycol), poly(propylene glycol) oligomers, a block copolymer of polyethylene glycol and polypropylene glycol, PTFE, ePTFE and derivatives and combinations thereof.

As discussed above, the coated medical device of the invention may comprise an additional coating layer such as an adherent layer, an additional layer comprising a therapeutic agent or a top coat layer. It should be noted that such additional layers are considered to be distinct and separate layers to the coating layer of the invention which comprises components i), ii) and iii). For example, while in one embodiment the coating layer of the invention (i.e. comprising components i), ii) and iii)) is surfactant-free, the medical device can have a distinct and separate coating layer comprising surfactant, either underlying or overlying the coating of the invention. Similarly, although in one embodiment the coating of the invention does not contain protein, the medical device may have a further coating layer, underlying or overlying the coating layer of the invention, which comprises protein.

As discussed above, a particular challenge when developing a solid drug coating for a medical device is to achieve a balance between having sufficient adhesion to the device such that the coating is not lost/damaged in transit, yet also having suitable release characteristics such that the drug will transfer from the coating to the target tissue i.e. if the adhesion of the coating is too strong, the coating will be durable but an insufficient amount of the drug will be released and will result in suboptimal efficacy. Conversely, a coating may have excellent release characteristics but if the coating does not have sufficient adhesion to the device then an insufficient amount of drug will reach the target tissue, and unintentional release of the drug in areas other than the target tissue may be detrimental to the patient.

The coating layer of the present invention provides a good balance of good adhesion to a medical device, thereby minimising or even eliminating coating loss during transit of the device, and suitable release characteristics such that the paclitaxel is delivered in an effective and efficient manner to the target tissue.

Paclitaxel-containing compositions of the invention were coated onto stent-grafts as described in Example 1 and were analysed in vitro for their ability to transfer paclitaxel from the device to the porcine tissue (as described in Example 3). Once removed from the porcine tissue the stent-grafts were analysed to determine the paclitaxel content remaining on the device, as described in Example 4. When compared with a comparator stent-graft with a coating of paclitaxel and urea, coatings of the invention were found to achieve higher uptake of paclitaxel into the vascular tissue and also higher paclitaxel content remaining on the spent device. This indicates higher efficiency in terms of paclitaxel uptake and also provides an indication of greater durability, because for devices of the invention a lower proportion of paclitaxel was lost (i.e. a greater proportion of the paclitaxel was accounted for as being transferred to the vascular tissue or remaining on the spent device).

Figure 5:
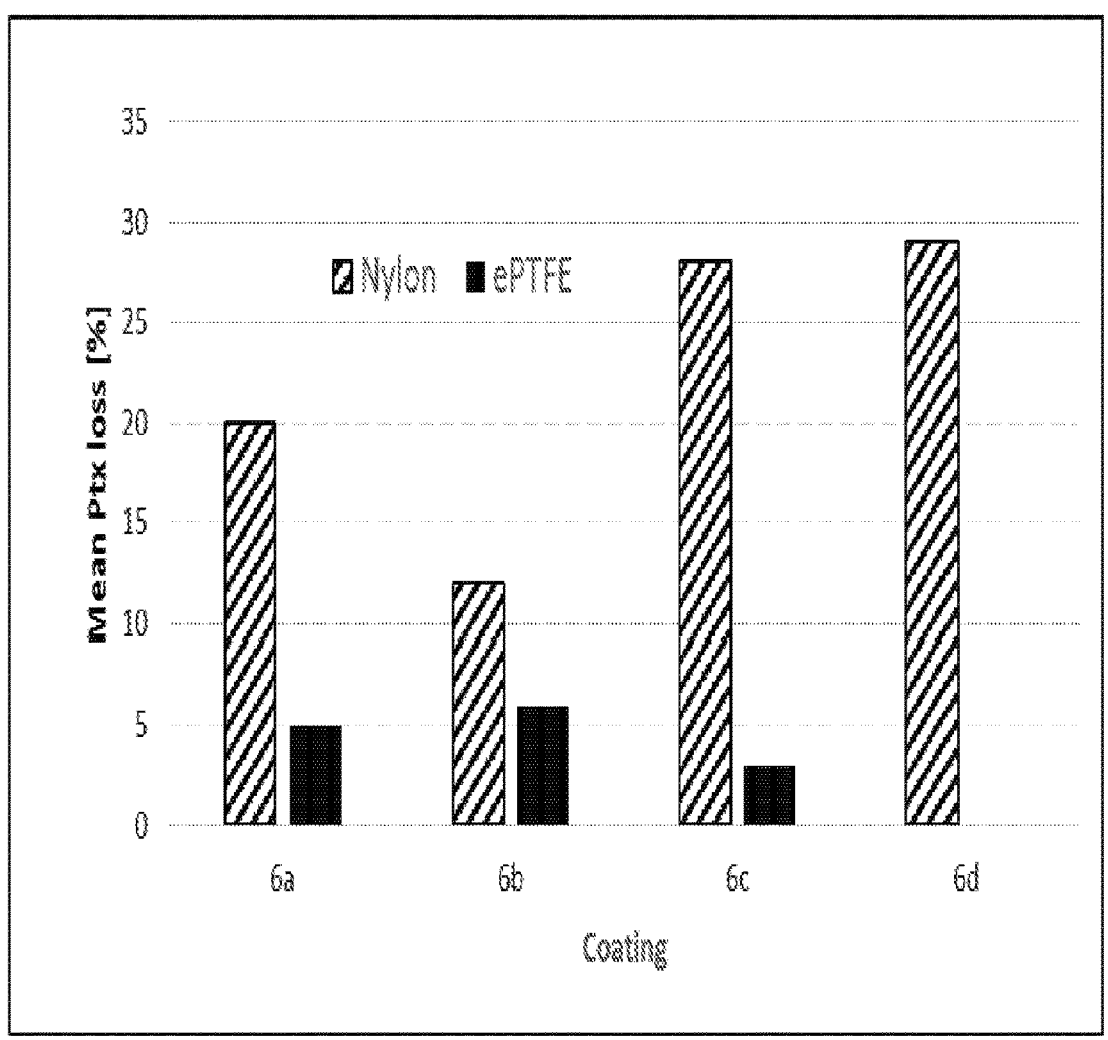
FIG. 5 shows the mean % of paclitaxel lost when balloons of the invention and a comparator were subjected to a shake test (Test Method Q) (Example 12).

Furthermore, in Example 12 the durability of the coated balloons of the invention was assessed using an adhesion test. The results of the experiment are summarised in FIG. 5 where it can be seen that coatings of the invention (6a-6c) generally exhibited better adherence compared with the comparator balloon having a coating of paclitaxel and urea (6d).

In one embodiment, the coating of the invention has suitable adherence such that less than 40% of the paclitaxel is lost during shaking, for example less than 30%, less than 25%, less than 20%, less than 15%, less than 10% or less than 5%, using Test Method Q, as described in Example 12.

Therapeutic Methods

Medical devices coated with the novel paclitaxel-excipient compositions of the invention are of use in medical therapy.

In one aspect of the invention is provided a medical device with a coating layer as described hereinabove for use in treating tissue in the human or animal body. The tissue to be treated includes any body cavity, space, or hollow organ passage(s) such as blood vessels, the urinary tract, the intestinal tract, nasal cavity, neural sheath, intervertebral regions, bone cavities, esophagus, intrauterine spaces, pancreatic and bile ducts, rectum, and those previously intervened body spaces that have implanted vascular grafts, stents, prosthesis, or other type of medical implants.

The medical device with a coating layer as described herein can be of use in the removal of obstructions such as emboli and thrombi from blood vessels, as a dilation device to restore patency to an occluded body passage, as an occlusion device to selectively deliver a means to obstruct or fill a passage or space, and as a centering mechanism for transluminal instruments like catheters.

In one aspect of the invention is provided a medical device with a coating layer as described hereinabove for use in the prevention or treatment of stenosis or restenosis in a blood vessel of the human body. In another aspect of the invention is provided a medical device with a coating layer as described hereinabove for use in the prevention or treatment of stenosis or restenosis in a blood vessel of the human body, where previously placed eluting constructs have failed. In another embodiment, a medical device with a coating layer as described herein can be used to establish or maintain arteriovenous access sites, e.g., those used during kidney dialysis.

In one embodiment, said medical device with a coating layer as described herein can be used for Percutaneous Transluminal Angioplasty (PTA) in patients with obstructive disease of the peripheral arteries. In another embodiment, said medical device comprises a medical balloon used for Percutaneous Transluminal Coronary Angioplasty (PTCA).

In another aspect of the invention is provided a method for the prevention or treatment of stenosis or restenosis (for example, coronary stenosis or restenosis) which comprises inserting transiently or permanently into said blood vessel in the human body a medical device with a coating layer as described hereinabove.

Paclitaxel-excipient solid compositions comprising components i), ii) and iii) as described hereinabove are of use in coating an exterior surface of a medical device, but may have further utility per se as pharmaceutical compositions.

The coated medical device of the invention will typically comprise a dose of paclitaxel. The dose of paclitaxel delivered will depend on many factors including the size of the coated area, the length of time the coated device is in contact with the target tissue and the amount of paclitaxel in the coating. Suitably the medical device has a coating layer containing an average of 0.1-10 µg/mm$^2$ of paclitaxel, such as 0.2-8 µg/mm$^2$, 0.5-5 µg/mm$^2$, or 1-4 µg/mm$^2$ e.g. 2 µg/mm$^2$, 3 µg/mm$^2$ or 4 µg/mm$^2$ of paclitaxel. The apparent coated surface area does not take account of porosity considerations of a porous substrate material. If the substrate material is porous, the effect of porosity on surface area is not considered for these calculations. For example, the apparent surface area of a cylindrical tubular ePTFE vascular graft (which is made of a porous material) with a paclitaxel-excipient coating of the invention comprising the inner surface of the tubular graft is calculated as it is for any cylindrical geometry as $2\pi rl$: where r is the graft inner radius; L is the axial length; and $\pi$ is the number pi. It is important to note that the porous nature of ePTFE and its effect on surface area is not accounted for herein. Accordingly, non-porous substrate materials that are cut into squares for analysis are taken to have a surface area of the length multiplied by the width.

The coated medical device of the invention will typically contain 0.01-300 mg of paclitaxel in total, for example 0.01-250 mg, 0.01-200 mg, 0.01-150 mg, 0.01-100 mg, 0.01-90 mg, 0.01-80 mg, 0.01-70 mg, 0.01-60 mg, 0.01-50 mg, 0.01-40 mg, 0.01-30 mg, 0.01-20 mg, 0.01-10 mg or 0.01-5 mg. In one embodiment, the coated medical device is a balloon and the coating layer contains 0.1-50 mg of paclitaxel in total. In one embodiment, the coated medical device is a stent and the coating layer contains 0.01-10 mg of paclitaxel in total. In one embodiment, the coated medical device is a stent graft and the coating layer contains 0.01-10 mg of paclitaxel in total.

The release characteristics of a composition of the invention may determine its suitability for a use in coating a particular type of medical device. Coatings of the invention which exhibit very fast release of paclitaxel are particularly suitable for use on DEBs, where once inflated the balloon is in contact with the target tissue for a relatively short amount of time before being removed. Conversely, a coating which exhibits relatively slower release of paclitaxel is better suited for use on a DES (or stent or stent graft (SSG)) which is retained within the vessel.

In one embodiment, the medical device of the invention has suitable paclitaxel release and tissue transfer characteristics such that using Test Method A-I or A-II as appropriate, the measured paclitaxel concentration in the tissue at the given time point is at least 1 µg drug per g tissue (µg/g), for example at least 2.5 µg/g, at least 5 µg/g, at least 10 µg/g, at least 50 µg/g or at least 100 µg/g.

In one embodiment, the medical device of the invention is a coated balloon and has suitable paclitaxel release and tissue transfer characteristics such that using Test Method A-I the measured paclitaxel concentration in the tissue at the 1 hr time point is at least 20 µg drug per g tissue (µg/g), for example at least 50 µg/g, at least 100 µg/g, at least 150 µg/g or at least 200 µg/g, as described in Example 8.

In one embodiment, the medical device of the invention is a stent-graft and has suitable paclitaxel release and tissue transfer characteristics such that using Test Method A-II the measured paclitaxel concentration in the tissue at the 24 hr time point is at least 1 µg drug per g tissue (µg/g), for example at least 10 µg/g, at least 50 µg/g or at least 100 µg/g, as described in Example 3.

In one embodiment, the medical device of the invention comprises a coating layer of immobilized heparin. The immobilized heparin layer may provide an antithrombogenic effect when the device is contacted with tissue. The bioactivity of the immobilized heparin layer can be analysed using Test Methods L and M. The amount of heparin immobilized on a device can be analysed using Test Method N.

In one embodiment, the medical device additionally comprises a coating layer of immobilized heparin and has HCII binding activity of greater than 1 pmol/cm$^2$ of surface according to Test Method L, before implantation, e.g. at least 5 pmol/cm$^2$.

In another embodiment, the medical device additionally comprises a coating layer of immobilized heparin and has ATIII binding activity of at least 1 pmol/cm$^2$ of surface according Test Method M, before implantation, e.g. at least 5 pmol/cm$^2$.

In another embodiment, the medical device additionally comprises a coating layer of immobilized heparin and has HCII binding activity of greater than 1 pmol/cm$^2$ of surface according to Test Method L, after elution of the paclitaxel, e.g. at least 5 pmol/cm$^2$.

In another embodiment, the medical device additionally comprises a coating layer of immobilized heparin and has ATIII binding activity of at least 1 pmol/cm$^2$ of surface according to Test Method M, after elution of the paclitaxel, e.g. at least 5 pmol/cm$^2$.

Methods for Preparing Compositions and Coatings of the Invention

Solid paclitaxel-excipient particulate compositions according to the invention can be prepared by a multitude of methods. One method of preparing a coating of the invention is by evaporation of one or more solutions of components i), ii) and iii). In one embodiment is provided a method comprising the steps of dissolving components i), ii) and iii) in one or more solvents to form one or more solutions, coating the device with each of the one or more solutions, and evaporating the solvent of each one or more solution. Suitably, the method comprises the step of dissolving components i), ii) and iii) in a solvent to form a solution, coating the device with the solution and evaporating the solvent. Solvents which may be used include water, acetone, alcohols (such as methanol, ethanol, propanol, isopropanol), tetrahydrofuran, DMF, DMSO, EtOAc, dioxane or mixtures thereof. Suitably the solvent is selected from water, acetone and mixtures thereof.

Suitably, the solution of the paclitaxel or components i), ii) and iii) is a solution in a solvent selected from water, acetone and mixtures thereof, for example between about 50/50 and 95/5, between about 60/40 and 90/10, between about 70/30 and about 90/10 or between about 70/30 and about 75/25 acetone/water (v/v), such as 90/10, 80/20, 75/25 or 70/30 acetone/water (v/v). In one embodiment, the solution of components i), ii) and iii) is 80/20 acetone/water (v/v).

Various methods for forming the coating of the invention by evaporation of a solutions of components i), ii) and iii) (or a single solution comprising components i), ii) and iii)) can be used. The solution(s) can be pipetted over the exterior surface of the device, which is itself under rotation, e.g. pipetting 90-100 ul of the coating solution over the device at a time. Alternatively, the device can simply be dipped into the solution(s), removed and then air dried. The dipping and drying process can be repeated as many times as is necessary to achieve the desired coating thickness or loading of paclitaxel. Other techniques such as casting, spinning, spraying, ink jet printing, electrostatic techniques, painting, dispersion coating, powder coating, or combinations thereof may be used to form the coating.

Following application of the coating a drying step may be required. The coating drying environment may be controlled as a function of time, such as by controlling/modulating the air composition, flow rate and flow patterns, air temperature, localized heating (e.g., heat lamp), etc, to thereby control physical properties of the coating.

A suitable procedure for forming a coating of the invention on a stent-graft via evaporation is described in Example 1, and a suitable procedure for forming a coating of the invention on a balloon via evaporation is described in Example 6.

In one embodiment, the coating comprises paclitaxel (component i)), ethylurea as component ii) and caffeine as component iii), and is formed by evaporation from a single solution comprising paclitaxel, ethylurea and caffeine. In this embodiment, suitably the weight % of paclitaxel in the pipetting/dipping solution (based on the total weight of solid components added) is between about 10 wt. % and about 95 wt. %, for example between about 40 wt. % and about 90 wt. %; between about 50 wt. % and about 90 wt. %, between about 60 wt. % and about 90 wt. %, between about 70 wt. % and about 90 wt. %, or between about 75 wt. % and about 85 wt. %. The weight % of ethylurea in the pipetting/dipping solution (based on the total weight of solid components added) is suitably between about 1 wt. % and about 95 wt. %, for example between about 5 wt. % and about 80 wt. %, between about 5 wt. % and about 50 wt. %; between about 5 wt. % and about 30 wt. %, between about 5 wt. % and about 20 wt. % or between about 5 wt. % and about 15 wt. %. The weight % of caffeine in the pipetting/dipping solution (based on the total weight of solid components added) is suitably between about 1 wt. % and about 95 wt. %, for example between about 5 wt. % and about 80 wt. %, between about 5 wt. % and about 50 wt. %; between about 5 wt. % and about 30 wt. %, between about 5 wt. % and about 20 wt. % or between about 5 wt. % and about 15 wt. %.

As used herein, weight percentage amounts of succinic acid, glutaric acid and caffeine are based on weight of succinic acid and glutaric acid as free acid and caffeine as free base.

In one embodiment, the coating comprises paclitaxel (component i)), ethylurea as component ii) and succinic acid as component iii), and is formed by evaporation from a single solution comprising paclitaxel, ethylurea and succinic acid. In this embodiment, suitably the weight % of paclitaxel in the pipetting/dipping solution (based on the total weight of solid components added) is between about 10 wt. % and about 95 wt. %, for example between about 40 wt. % and about 90 wt. %; between about 50 wt. % and about 90 wt. %, between about 60 wt. % and about 90 wt. %, between about 70 wt. % and about 90 wt. %, or between about 75 wt. % and about 85 wt. %. The weight % of ethylurea in the pipetting/dipping solution (based on the total weight of solid components added) is suitably between about 1 wt. % and about 95 wt. %, for example between about 5 wt. % and about 80 wt. %, between about 5 wt. % and about 50 wt. %; between about 5 wt. % and about 30 wt. %, between about 5 wt. % and about 20 wt. % or between about 5 wt. % and about 15 wt. %. The weight % of succinic acid in the pipetting/dipping solution (based on the total weight of solid components added) is suitably between about 1 wt. % and about 95 wt. %, for example between about 5 wt. % and about 80 wt. %, between about 5 wt. % and about 50 wt. %; between about 5 wt. % and about 30 wt. %, between about 5 wt. % and about 20 wt. % or between about 5 wt. % and about 15 wt. %.

In one embodiment, the coating comprises paclitaxel (component i)), ethylurea as component ii) and glutaric acid as component iii), and is formed by evaporation from a single solution comprising paclitaxel, ethylurea and glutaric acid. In this embodiment, suitably the weight % of paclitaxel in the pipetting/dipping solution (based on the total weight of solid components added) is between about 10 wt. % and about 95 wt. %, for example between about 40 wt. % and about 90 wt. %; between about 50 wt. % and about 90 wt. %, between about 60 wt. % and about 90 wt. %, between about 70 wt. % and about 90 wt. %, or between about 75 wt. % and about 85 wt. %. The weight % of ethylurea in the pipetting/dipping solution (based on the total weight of solid components added) is suitably between about 1 wt. % and about 95 wt. %, for example between about 5 wt. % and about 80 wt. %, between about 5 wt. % and about 50 wt. %; between about 5 wt. % and about 30 wt. %, between about 5 wt. % and about 20 wt. % or between about 5 wt. % and about 15 wt. %. The weight % of glutaric acid in the pipetting/dipping solution (based on the total weight of solid components added) is suitably between about 1 wt. % and about 95 wt. %, for example between about 5 wt. % and about 80 wt. %, between about 5 wt. % and about 50 wt. %; between about 5 wt. % and about 30 wt. %, between about 5 wt. % and about 20 wt. % or between about 5 wt. % and about 15 wt. %.

As used herein, weight percentage amounts of paclitaxel are based on weight of anhydrous paclitaxel (i.e. ignoring any associated water in the case of hydrates of paclitaxel).

A coating of the invention may be applied to a medical device using a method which involves minimal solvent, or indeed no solvent. For example, a dry powder method may be used which involves preparing components i), ii) and iii) in powder form, and then applying the powder forms to the device, with optional subsequent steps of thermal treatment. A variant of the method involves combining components i), ii) and iii) in powder form, and then applying the powder to the device and optionally applying a subsequent thermal treatment step.

The powder forms of components i), ii) and iii) (or single powder form of combined components i), ii) and iii)) is suitably sprayed on to the device, which optionally comprises an adhesive layer (as described hereinabove), which may be followed by thermal treatment, for example, to affix the layer to the surface of the device.

Also provided is a process for preparing a coating layer on a surface of a medical device which comprises the steps of:
a) dissolving components i), ii) and iii) in one or more solvents to form one or more solutions,
   wherein
   component i) is a therapeutic agent which is paclitaxel; and
   component ii) is urea or a pharmaceutically acceptable salt thereof, or a urea derivative or a pharmaceutically acceptable salt thereof; and
   component iii) is succinic acid, glutaric acid or caffeine, or a pharmaceutically acceptable salt of any one thereof; and
b) coating a surface of the device with each of the said one or more solutions of step a); and
c) evaporating the solvent.

Also provided is a process for preparing a coating layer on a surface of a medical device which comprises the steps of:

a) dissolving components i), ii) and iii) in a solvent to form a solution, wherein component i) is a therapeutic agent which is paclitaxel; and component ii) is urea or a pharmaceutically acceptable salt thereof or a urea derivative or a pharmaceutically acceptable salt thereof; and component iii) is succinic acid, glutaric acid or caffeine, or a pharmaceutically acceptable salt of any one thereof; and b) coating a surface of the device with the solution of step a); and c) evaporating the solvent.

Also provided is a process for preparing a coating layer on a surface of a medical device which comprises the steps of:

a) dissolving components i), ii) and iii) in one or more solvents to form one or more solutions, wherein component i) is a therapeutic agent which is paclitaxel; and component ii) is urea or a derivative thereof; and component iii) is succinic acid, glutaric acid or caffeine; and b) coating a surface of the device with each of the said one or more solutions of step a); and c) evaporating the solvent.

Also provided is a process for preparing a coating layer on a surface of a medical device which comprises the steps of:

a) dissolving components i), ii) and iii) in a solvent to form a solution, wherein component i) is a therapeutic agent which is paclitaxel; and component ii) is urea or a derivative thereof; and component iii) is succinic acid, glutaric acid or caffeine; and b) coating a surface of the device with the solution of step a); and c) evaporating the solvent.

Embodiments described above with respect to the method embodiments are equally applicable to the process embodiments.

Typically, in an embodiment, the coating of the invention will have an average total thickness of about 0.1 µm to about 200 µm, such as about 0.2 µm to about 100 µm. In the case of porous materials, the aforementioned thickness refers to the thickness above the surface of the porous material (the coating in pores would constitute additional thickness not accounted for in these figures). Coating thickness can be measured using a suitable coating thickness analyser, gauge, by SEM or by XPS analysis (see Evaluation Methods).

It should be noted that the methods of preparing the coating layer or composition of the invention described above (e.g. dry powder methods and solvent evaporation methods) are all equally suitable for preparing the various coating and composition embodiments described hereinabove.

It should also be noted that medical devices prepared according to the methods and processes described herein are also considered to form part of the present invention.

Further Embodiments of the Invention

In one aspect is provided a medical device for delivering a therapeutic agent to a tissue, the device having a coating layer applied to a surface of the device, the coating layer comprising components i), ii) and iii), wherein component i) is a therapeutic agent which is paclitaxel; and
component ii) is urea or a derivative thereof; and
component iii) is succinic acid, glutaric acid or caffeine.

In another aspect is provided a composition comprising a mixture of components i), ii) and iii), wherein
component i) is paclitaxel; and
component ii) is urea or a derivative thereof; and
component iii) is succinic acid, glutaric acid or caffeine.

In one aspect is provided a medical device for delivering a therapeutic agent to a tissue, the device having a coating layer applied to a surface of the device, the coating layer comprising a mixture of components i), ii) and iii), wherein
component i) is a therapeutic agent which is paclitaxel; and
component ii) is methyl urea, ethylurea or propyl urea; and
component iii) is succinic acid, glutaric acid or caffeine.

In one aspect is provided a medical device for delivering a therapeutic agent to a tissue, the device having a coating layer applied to a surface of the device, the coating layer comprising a mixture of components i), ii) and iii), wherein
component i) is a therapeutic agent which is paclitaxel; and
component ii) is ethyl urea; and
component iii) is succinic acid, glutaric acid or caffeine.

In one aspect is provided a medical device for delivering a therapeutic agent to a tissue, the device having a coating layer applied to a surface of the device, the coating layer comprising a mixture of components i), ii) and iii), wherein
component i) is a therapeutic agent which is paclitaxel; and
component ii) is ethyl urea; and
component iii) is caffeine.

In one aspect is provided a medical device for delivering a therapeutic agent to a tissue, the device having a coating layer applied to a surface of the device, the coating layer comprising a mixture of components i), ii) and iii), wherein
component i) is a therapeutic agent which is paclitaxel; and
component ii) is ethyl urea; and
component iii) is succinic acid or glutaric acid.

In one aspect is provided a medical device for delivering a therapeutic agent to a tissue, the device having a coating layer applied to a surface of the device, the coating layer comprising a mixture of components i), ii) and iii), wherein
component i) is a therapeutic agent which is paclitaxel; and
component ii) is ethyl urea; and
component iii) is succinic acid.

In one aspect is provided a medical device for delivering a therapeutic agent to a tissue, the device having a coating layer applied to a surface of the device, the coating layer comprising a mixture of components i), ii) and iii), wherein
component i) is a therapeutic agent which is paclitaxel; and
component ii) is ethyl urea; and
component iii) is glutaric acid.

In one aspect is provided a medical device for delivering a therapeutic agent to a tissue, the device having a coating layer applied to an exterior surface of the device, said device being composed of a material selected from nylon and a fluoropolymer, the coating layer comprising a mixture of components i), ii) and iii), wherein
component i) is a therapeutic agent which is paclitaxel; and
component ii) is ethyl urea; and
component iii) is succinic acid, glutaric acid or caffeine.

In another aspect of the invention is provided a medical device for delivering a therapeutic agent to a tissue, the device having a coating layer applied to an exterior surface of the device, the coating layer comprising a mixture of components i), ii) and iii), wherein
component i) is a therapeutic agent which is paclitaxel; and
component ii) is ethyl urea; and
component iii) is succinic acid, glutaric acid or caffeine; and wherein the paclitaxel, when formulated in the coating layer, is stable to ethylene oxide sterilization.

In another aspect of the invention is provided a medical device for delivering a therapeutic agent to a tissue, the device having a coating layer applied to an exterior surface of the device, the coating layer comprising a mixture of components i), ii) and iii), wherein
component i) is a therapeutic agent which is paclitaxel; and component ii) is ethyl urea; and
component iii) is succinic acid, glutaric acid or caffeine;
wherein the coating layer is formed by evaporation of a solution of components i), ii) and iii).

Coatings and compositions according to the present invention are expected to have one or more of the following merits or advantages:
- suitable paclitaxel release and tissue transfer characteristics, e.g. as measured in Test Method A-I or Test Method A-II;
- good adherence to a medical device e.g. as measured using Test Method Q;
- good stability of the paclitaxel, when formulated in the coating, to sterilization e.g. as measured using Test Method E (ethylene oxide sterilization), as measured using Test Method F (electron beam sterilization), as measured using Test Method G (vapour hydrogen peroxide sterilization) or Test Method H (plasma hydrogen peroxide sterilization);
- compatibility with additional therapeutic agents, such as heparin; and compatibility with a range of substrate materials conventionally used in the manufacture of medical devices.

The invention embraces all combinations of indicated groups and embodiments of groups recited above.

All patents and patent applications referred to herein are incorporated by reference in their entirety.

Percentage values given in this specification are based on weight unless otherwise indicated.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

| Definitions and Abbreviation | |
|---|---|
| DEB | drug eluting balloon |
| DES | drug eluting stent |
| DSC | differential scanning calorimetry |
| ePTFE | expanded polytetrafluoroethylene |
| h | hour |
| HPLC | high-performance liquid chromatography |
| ND | not determined |
| N/T | not tested |
| PEG | polyethylene glycol |
| PBS | phosphate buffered saline |
| Ptx | paclitaxel |
| SEM | sacnning electron microscopy |
| SSG | stent or stent graft |
| UPLC | ultra-performance liquid chromatography |

Examples

General Procedures
Chemicals

Anhydrous crystalline paclitaxel was purchased from Indena. Anhydrous Caffeine USP 98.5-101.0% was purchased from Spectrum chemicals MFG or Sigma-Aldrich Corporation. Succinic acid ACS Reagent, ≥99.0% was purchased from Sigma-Aldrich. Glutaric acid was purchased from Spectrum chemicals MFG or Sigma-Aldrich Corporation. Ethylurea was purchased from Aldrich and Urea from Sigma-Aldrich.

Solvent

Acetone ("dry" with <0.5% water) was purchased from Sigma. In all cases where water is mentioned, deionized water was used.

Materials

GORE® VIABAHN® Endoprostheses with Heparin Bioactive Surface are stent-grafts with an immobilized heparin coating with dimensions of 6 mm in diameter and 50 mm in length, and 7 mm diameter and 50 mm in length, and were obtained from W. L. Gore and Associates Inc.

Nylon balloon catheters having dimensions of 5 mm in diameter and 40 mm in length were obtained (Bavaria Medizin Technologie, Weßling, Germany, model # BMT-035, article #08GL-504A, 5×40 mm). The balloons have the following specifications: 6 atmosphere (atm) nominal inflation pressure and a 14 atm. rated burst pressure, a 5 mm nominal diameter, 40 mm balloon working length, mounted on a 0.9 mm guidewire compatible catheter.

ePTFE balloons with dimensions 6×40 mm were obtained from W. L. Gore & Associates, Inc. A method for constructing an ePTFE balloon is provided in Example 5.

Porcine carotid arteries were obtained from Animal Technologies Inc. (Tyler, Tex.) and Lövsta Kött AB (Uppsala, Sweden). Luer fittings (#11570) were purchased from Qosina (Edgewood, N.Y.).

Evaluation Methods

The parameter being evaluated by each method is given in parentheses.

Ultra-Performance Liquid Chromatography (UPLC) Analysis

Paclitaxel Concentration

UPLC analysis is carried out using a Waters instrument (model # ACQUITY H-class). The identification of paclitaxel is determined by the retention time of paclitaxel. The concentration of paclitaxel is directly proportional to the integrated peak area, determined by external standardization. Samples with solid paclitaxel is submerged in an extraction solvent and sonicated for 15 minutes. Samples are further diluted to concentrations within the calibration range using a sample diluent. Paclitaxel standards of 0.05-30 µg/ml are prepared by serial dilution of pure paclitaxel dissolved in the sample diluent. All samples and standards are protected from light during preparation. UPLC chromatography parameters are: phenyl column (1.7 um, 2.1×50 mm); mobile phase water:acetonitrile; flow rate 0.7 ml/min; run time 10 min; injection volume 3 ul; purge solvent acetonitrile:water (10:90 v/v); wash solvent isopropanol; column temperature 35° C.; UV detector wavelength 227.0±1.2 nm; sample rate 20 points/sec.

Degradation Products of Paclitaxel (Example 13)

Chromatographic analysis of related substances, typically degradation products, are performed using a Waters instrument (model # ACQUITY I-class). The identification of paclitaxel and related substances are determined by their respective retention times. The concentration of each component is directly proportional to the integrated peak area, determined by external standardization. The related substances screened for are listed in the USP Paclitaxel Related Compound A RS. UPLC chromatography parameters are: C18 column (1.7 um, 2.1×100 mm); mobile phase 20 µM ammonium acetate buffer:acetonitrile; flow rate 0.5 ml/min; run time 10 min; injection volume 3-10 ul; purge solvent acetonitrile:water (10:90 v/v); wash solvent isopropanol;

column temperature 35° C.; UV detector wavelength 227.0±1.2 nm; sample rate 20 points/sec.

Scanning Electron Microscopy with Energy Dispersive X-Ray Spectroscopy (Coating Coverage and Uniformity)

SEM images of coated devices of the invention can be evaluated using a Hitachi TM3000 table top SEM.

X-Ray Photoelectron Spectroscopy with Depth Profiling (XPS) (Coating Thickness)

X-ray Photoelectron Spectroscopy (XPS or ESCA) is the most widely used surface characterization technique providing non-destructive chemical analysis of solid materials. Samples are irradiated with mono-energetic X-rays causing photoelectrons to be emitted from the top 1-10 nm of the sample surface. An electron energy analyzer determines the binding energy of the photoelectrons. Qualitative and quantitative analysis of all elements except hydrogen and helium is possible, at detection limits of ~0.1-0.2 atomic percent. Analysis spot sizes range from 10 μm to 1.4 mm. It is also possible to generate surface images of features using elemental and chemical state mapping. Depth profiling is possible using angle-dependent measurements to obtain non-destructive analyses within the top 10 nm of a surface, or throughout the coating depth using destructive analysis such as ion etching.

Test Methods

Test Method a—In Vitro Tissue Transfer and Uptake Test of Paclitaxel

Coated medical devices are examined for their ability to transfer paclitaxel from the device surface to vascular tissue in an in vitro model essentially as described by Liao (D. Liao et al., Biochem Biophys Res Commun, 372(4): 668-673, 2008. "Vascular smooth cell proliferation in perfusion culture of porcine carotid arteries").

Test Method A-I—Balloons

Porcine carotid arteries from 6-9 month old pigs, approximately 6 cm in length, were trimmed of adipose tissue, and fitted at their distal end with Luer fittings using wax thread. The vessel diameters at the proximal and distal ends were approximately 5 mm and 2 mm, respectively (vessels tapered as a function of length). They were flushed with 12 ml of PBS and pinned to a dissecting pad under a slight axial stretch to straighten the vessel. The coated balloons, all 5×40 mm (diameter×length) compacted according to Test Method I-I, were inserted into the proximal ends of the vessels to the middle of the vessel, held at this position for 30 sec, and deployed and removed according to Test Method I-II. A Luer fitting was fitted to the proximal end with wax thread. Tubing was connected to the proximal and distal fittings, and the vessel was flushed with PBS at 60 ml/min for 1 hr at 37° C. The flow was stopped and the vessel analyzed for paclitaxel content as described below in Test Method D.

Test Method A-I—Stents and Stent-Grafts

Porcine carotid arteries from 6-9 month old pigs, approximately 6 cm in length, were trimmed of adipose tissue, and fitted at their distal end with Luer fittings using wax thread. The vessel diameters at the proximal and distal ends were approximately 5 mm and 2 mm, respectively (vessels tapered as a function of length). They were flushed with 12 ml of PBS and pinned to a dissecting pad under a slight axial stretch to straighten the vessel. The coated stent or stent-graft was compacted diametrically according to Test Method J-I. The compacted stents or stent-grafts were inserted into the proximal end of the porcine vessel to the middle of the vessel, and deployed to their expanded state according to Test Method J-II. A Luer fitting was attached to the proximal end and distal ends of the vessel with wax thread. Tubing was connected to the proximal and distal fittings, and the vessel was flushed with PBS at 60 ml/min for 24 hr at 37° C. The stent or stent-graft was removed, and vessel analysed for paclitaxel content as described below in Test Method D.

Test Method B—Determining Paclitaxel Content Following Manipulation

These tests allow the amount of paclitaxel on the coated device to be determined. By comparing the amount of paclitaxel on the device before and after device manipulation, the durability of the coating can be assessed.

Test Method B-I—Weight

The coated device is weighed before and after manipulation (e.g. manipulation according to Test Methods I or J). The weight of the coating lost during manipulation can therefore be determined. In cases where the coating composition prior to manipulation is known, the weight of paclitaxel lost can calculated, as can the % of paclitaxel lost, and the % of paclitaxel remaining on the device.

Test method B-II—Extraction

The device is manipulated (e.g. according to Test Methods I or J) and then the paclitaxel remaining on the device following manipulation is extracted by immersing the device in acidified methanol (0.2% v/v acetic acid in 5 mL methanol) for 15 minutes. The paclitaxel-containing methanol solution is evaluated using UPLC analysis (as described in Evaluation Methods) to determine the paclitaxel content. This can be compared with the known loading of paclitaxel on the device prior to manipulation, and the % paclitaxel lost, and the % of paclitaxel remaining on the device may be calculated.

Test Method C—In Vitro Evaluation of Paclitaxel Elution Profile

A method may be used to study the release rate of paclitaxel from the device in vitro, in particular the profile of accelerated elution. For this purpose, the coated device is put in a solution of a suitable buffer at a fixed temperature. The eluted paclitaxel is dissolved in the aqueous buffer solution containing cyclodextrin which increases the solubility of paclitaxel in water up to the necessary concentration. By withdrawing samples at chosen time points, analysing the paclitaxel content by UPLC techniques (as described in Evaluation Methods and Test Method B-III) for paclitaxel content and plotting of paclitaxel content against time, an elution profile can be created.

Test Method D—In Vivo Evaluation of Paclitaxel Transfer—Balloon

Coated balloons were deployed in a porcine model in an in vivo test employing the peripheral arteries in an adult swine. Angiography of the peripheral artery determined balloon inflation pressure required for appropriate vessel over-sizing. The balloon was tracked to the target site, inflated to the required inflation pressure for 60 seconds, deflated and removed. Post-deployment, the spent device was submitted for UPLC analysis of remaining paclitaxel content as described in the Evaluation Methods.

Animals were euthanized after 1 day or after 29 days. The treated arteries were harvested. Adipose tissue was removed from each artery, radial cross-sections (100±50 mg) were cut from each artery, and the arteries analyzed for paclitaxel content using UPLC/tandem mass spectrometry. For the treated artery, mean paclitaxel levels were calculated by averaging paclitaxel levels in all radial cross-sections in the indicated segment.

The tissue samples were homogenized and extracted with 0.2% acetic acid in methanol, containing 2 mg/ml deuterated paclitaxel as an internal standard. The samples were centrifuged to remove all particulates and the supernatant was used for the analysis by UPLC (Evaluation Methods)

For each treated artery, mean drug concentrations in the proximal, treated, distal, and remote segments were calculated as the average drug concentration of all sections in the indicated segment. Treatment means were then calculated by averaging the segment means with n=3 arteries for each treatment group.

Test Method E—Stability to Ethylene Oxide

The medical device of the invention is placed in a breathable polyethylene pouche (e.g. a Tyvek pouch) and subjected to at least 12 hours preconditioning at 50° C. and 60% relative humidity followed by 2 hours exposure of ethylene oxide at a pressure of 366 mBar and 50° C. The chamber is then be degassed at 50° C. for at least 10 hours. Sterilization by ethylene oxide may be performed at Synergy Health Ireland Ltd.

After sterilization, the paclitaxel content on the device is assessed (through device extraction i.e. immersion of the whole device in an extraction solvent) using UPLC quantification as described in the evaluation methods section. For each device, the percentage paclitaxel recovery after sterilization can be calculated by normalizing the extracted paclitaxel amount by the theoretical paclitaxel amount loaded on the device pre-sterilization as described for Test Method B-II.

Test Method F—Stability to Electron Beam Sterilization

A further method to sterilize a medical device of the invention is electron beam sterilization. The device is placed into a breathable polyethylene pouch (e.g. a Tyvek pouch) and irradiated at a dosage of 15 to 40 kGray under ambient conditions, using commercial sterilization providers, such as Sterigenics International, Inc. (Deerfield, Ill.). After e-beam sterilization, the paclitaxel content on the device may be assessed as described for Test Method B-II.

Test Method G—Stability to Vapour Hydrogen Peroxide Sterilization

A further method to sterilize a medical device of the invention is vapour hydrogen peroxide sterilization. The device is placed into a breathable polyethylene pouch (e.g. a Tyvek pouch) and exposed to vapour hydrogen peroxide using a commercially available sterilization chamber, such as the VHP-MD880 system (Steris Corp., Mentor, Ohio) following the manufacturer's recommended protocol. After vapour hydrogen peroxide sterilization, the paclitaxel content on the device is assessed as described for Test Method B-II.

Test Method H—Stability to Plasma Hydrogen Peroxide Sterilization

A further method to sterilize a medical device of the invention is plasma phase hydrogen peroxide sterilization. The implantable medical device is placed into a breathable polyethylene pouch (e.g. a Tyvek pouch) and exposed to plasma phase hydrogen peroxide using a commercially available sterilization chamber, such as the Sterrad 100NX system (Advanced Sterilization Products, Irvine, Calif.) following the manufacturer's recommended protocol. After plasma phase hydrogen peroxide sterilization, the paclitaxel content on the device may be assessed as described for Test Method B-II.

Test Methods I-I, I-II, J-I and J-II Manipulation of Balloons, Stents and Stent-Grafts The impact of manipulation on a balloon, stent or stent-graft (e.g. during typical manufacturing processing and then implantation) can be assessed by comparing, for example, the weight of the entire balloon, stent or stent-graft before and after manipulation, or the amount of paclitaxel on the balloon, stent or stent-graft before and after manipulation (using Test Method B-I or B-II). Balloons are manipulated according to Test Method I-I, or Test Method I-I followed by Test Method I-II, and stents and stent-grafts are manipulated according to Test Method J-I, or Test Method J-I followed by Test Method J-II.

Test Method I-I—Compaction and Constraining of Balloons

Balloons are compacted diametrically to an outer diameter of 3.36 mm using means known to those of skill in the art of self-expanding stents and stent-grafts. Once compacted the balloons are constrained in the compacted state within a constraint tube with an inner diameter of 3.6 mm.

Test Method I-II—Deployment of Balloons

Balloons are deployed by inflating the balloons using a deployment system that uses water to inflate the balloons to a pressure of 6 atm. The pressure is held for 1 minute prior to release of the pressure and careful removal of the balloon.

Test Method J-I—Compaction and Constraining of Stents and Stent-Grafts

Stent or stent-grafts are compacted diametrically to an outer diameter of 3.0 mm using means known to those of skill in the art of self-expanding stent-grafts. Once compacted, stent or stent-grafts are constrained in the compacted state within a constraint tube with an inner diameter of 3.0 mm.

Test Method J-II—Deployment of Stent or Stent-Grafts

Stent or stent-grafts are deployed by pulling them out of the constraint tube using attached wax threads.

Test Method K—Blood Contact Evaluation (Platelet Loss)

Medical devices of the invention, in particular those comprising a heparin coating may be analyzed by performing blood contact evaluation, to evaluate their thromboresistant properties.

A procedure which may be used when the medical device is a stent-graft is as follows. Firstly the stent-graft is washed with 0.15M saline solution for 15 min to ensure complete wetting. The wetted stent-graft is placed in heparinized PVC tubing containing whole blood and left to rotate in a circulating loop at 20 rpm (see Ekdahl K. N., Advances in Experimental Medicine and Biology, 2013, 735, 257-270 for a representative procedure). The platelets from fresh blood and from the blood collected from the tubes are counted in a cell counter to measure the loss of platelets. A great loss of platelets indicates poor thromboresistant performance of the device, in particular of the first coating layer. Conversely a minimal loss of platelets indicates a thromboresistant device, in particular with a thromboresistant first coating layer.

The negative control is an empty loop of heparinized PVC without any device. This represents a thromboresistant control for which the incubated blood should only demonstrate a minimal loss of platelets. The positive control is an empty loop of non-heparinized PVC without any device. This represents a thrombogenic control for which a great loss of platelets should be observed. The controls are included for ensuring the quality of the experiment and the blood.

Test Method L—Evaluation of Heparin Bioactivity Via HCII Binding Activity (Quantitative Heparin Function)

For medical devices of the invention which comprise a heparin coating, the heparin bioactivity of the device can be measured according to WO2009/064372 (Gore Enterprise Holdings, Inc.; incorporated herein by reference) by measuring the ability, or capacity, of the heparin to bind a known quantity of heparin cofactor II (HCII), using an assay as described by Larsen M. L., et al., in "Assay of plasma heparin using thrombin and the chromogenic substrate H-D-Phe-Pip-Arg-pNA (S-2238)." Thromb Res 13:285-288 (1978) and Pasche B., et al., in "A binding of antithrombin to immobilized heparin under varying flow conditions."

Artif. Organs 1991; 15:281-491). The results are expressed as picomoles heparin cofactor II (HCII) bound per apparent square centimetre of device surface (pmol HCII/cm² device surface). The apparent device surface area does not take into account multiple covered surfaces nor porosity considerations of a device composed of a porous material. If the surface of the device is porous, the effect of porosity on surface area is not considered for these calculations. For example, the apparent surface area of a cylindrical tubular ePTFE vascular graft (which is made of a porous material) with heparin immobilized on substrate material comprising the inner surface of the tubular graft is calculated as it is for any cylindrical geometry as $2\pi rL$: where r is the graft inner radius; L is the axial length; and $\pi$ is the number pi.

Test Method M—Evaluation of Heparin Bioactivity Via ATIII Binding Activity (Quantitative Heparin Function)

For medical devices of the invention which comprise a heparin coating, the heparin bioactivity of the device can be measured by measuring the ability, or capacity, of the heparin to bind antithrombin III (ATIII) as described by Pasche, et al. in "A binding of antithrombin to immobilized heparin under varying flow conditions" (Artif. Organs 1991; 15:281-491) and Larsen M. L., et al. in "Assay of plasma heparin using thrombin and the chromogenic substrate H-D-Phe-Pip-Arg-pNA" (S-2238) (Thromb. Res. 1978; 13:285-288). Washed samples are incubated with an excess antithrombin in solution to saturate all available antithrombin-binding sites of the heparin surface. Non-specifically adsorbed antithrombin is rinsed away using a salt solution. Subsequently, antithrombin specifically bound to the surface bound heparin is released by incubating with a solution of heparin at high concentration. Finally, the antithrombin released from the heparin-surface is measured in a thrombin inhibition assay, based on a chromogenic thrombin substrate. The results are expressed as picomoles antithrombin III (ATIII) bound per apparent square centimetre of device (pmol ATIII/cm² device surface). The apparent device surface area does not take into account multiple covered surfaces nor porosity considerations of a device composed of a porous material. If the surface of the device is porous, the effect of porosity on surface area is not considered for these calculations. For example, the apparent surface area of a cylindrical tubular ePTFE vascular graft (which is made of a porous material) with heparin immobilized on substrate material comprising the inner surface of the tubular graft is calculated as it is for any cylindrical geometry as $2\pi rL$: where r is the graft inner radius; L is the axial length; and $\pi\pi$ is the number pi.

Test Method N—Evaluation of Heparin Density (Quantitative Heparin Attachment)

Quantification of surface immobilized heparin can be performed by complete degradation of heparin followed by colorimetric determination of the reaction products released into solution. Degradation is achieved by reacting the heparin surface with an excess of sodium nitrite under acidic conditions. The degradation products, mainly disaccharides, are quantified colorimetrically in a reaction with MBTH (3-methyl-2-bezotiazolinon hydrazone hydrochloride), essentially as described in Smith R. L. and Gilkerson E (1979), Anal Biochem 98, 478-480, which is incorporated herein by reference in its entirety.

Test Method O—Staining Techniques

Devices of the invention can be subjected to toluidine blue stain solution (200 mg/L in water) by immersing in the solution for 2 minutes followed by extensive water rinse. A blue or violet colour is observed on surfaces that contain a net negative charge e.g. immobilized heparin moiety.

Test Method P—Surface Biocompatibility

The biocompatibility of a surface of an implantable medical device of the invention can be assessed as described in Lappegard, K. T 2008, J. Biomed. Mater. Res. Vol 87, 129-135 (incorporated herein by reference). A procedure which may be used to evaluate the inflammatory response of a stent or stent-graft of the invention following removal of the Paclitaxel coating (according to Test Method B-III) is as follows. Firstly the stent or stent-graft is washed with 0.15 M saline solution for 15 min. The washed stent or stent-graft is placed in heparinized PVC tubing containing whole blood and left to rotate in a circulating loop at 20 rpm (see Ekdahl K. N., Advances in Experimental Medicine and Biology, 2013, 735, 257-270 (incorporated herein by reference) for a representative procedure). After incubation, the blood is centrifuged for 15 min, 3220 g at 4° C. The plasma is frozen in aliquots at −70° C. for later analysis of cytokines. Plasma samples are analyzed using multiplex cytokine assay (Bio-Plex Human Cytokine 27-Plex Panel, Bio-Rad Laboratories, Hercules, Calif.) according to the method described by Lappegard et al. (above).

The negative control is an empty loop of heparinized PVC without any device. This represents a non-inflammatory control for which the incubated blood should demonstrate no or minimal amount of inflammatory markers. The positive control is an empty loop of non-heparinized PVC without any device. This represents an inflammatory control for which a great amount of inflammatory markers should be observed. The controls are included for ensuring the quality of the experiment and the blood.

Test Method Q—Shake Test (Coating Adherence)

The coating adherence to the device can be evaluated in a shake test. Coated devices are placed in a 15 mL Falcon test tube and tapped against the bottom of the test tube for 30 seconds to stress the sample. Loosely bound coating will fall off the surface of the device and into the test tube. The paclitaxel content of the material in the test tube is evaluated using UPLC analysis (Evaluation Methods). The coating adherence is measured in percent of paclitaxel lost following shaking relative to the theoretical loading of paclitaxel on the device.

Example 1: Method for Preparing Coating of the Invention—Stent-Grafts

GORE® VIABAHN® Endoprostheses with Heparin Bioactive Surface (as described in "Materials") are stent-grafts which have been pre-coated with a coating layer of immobilized heparin. The pre-coated stent-grafts were over-coated using the following general procedure: Coating formulations of the invention containing paclitaxel, ethyl urea and caffeine; paclitaxel, ethyl urea and succinic acid; and paclitaxel, ethyl urea and glutaric acid were prepared by dissolving the paclitaxel, ethyl urea and caffeine or succinic acid or glutaric acid, as appropriate, in acetone/water (80/20 (v/v)). Each coating solution was then applied to a pre-coated stent-graft in expanded form, as follows. The stent-grafts were coated at the proximal end (covering the portion up to 5 mm from the proximal end) by dispensing the coating solution (using a syringe pump and set to a dispensing speed of 15 uL/min while moving the needle 1 mm post each dispensing step) under 200 rpm rotation.

The components of each formulation are shown in Table 1 and specific methods described in Examples 1a, 1b and 1c below.

As a comparative example, a coating solution containing paclitaxel and urea was prepared as described in Example 2d.

The final paclitaxel loading on the coated area for all devices was approximately 6.37 µg/mm$^2$ (estimated by dispensing a known solution volume with a known paclitaxel concentration).

TABLE 1

Coating formulations for preparing stent-grafts of the invention (1a-1c) and comparator (1d)

| Example | Ptx [mg] | Ethyl urea [mg] | Caffeine [mg] | Succinic acid [mg] | Glutaric acid [mg] | Urea [mg] | Acetone [mL] | Water [mL] |
|---|---|---|---|---|---|---|---|---|
| 1a | 95 | 12 | 12 | — | — | — | 4 | 1 |
| 1b | 95 | 12 | — | 12 | — | — | 4 | 1 |
| 1c | 95 | 12 | — | — | 12 | — | 4 | 1 |
| 1d | 80 | — | — | — | — | 20 | 4 | 1 |

Example 1a: Coating of the Invention Containing Paclitaxel (100 µg Loading), Caffeine and Ethyl Urea—Stent-Graft 95 mg of paclitaxel, 12 mg of ethyl urea and 12 mg of caffeine were added to a glass vial. A mixture of acetone (4 mL) and water (1 mL) was added to form a solution which was allowed to dissolve while stirring at room temperature. The resulting coating solution (19 mg paclitaxel/mL) was applied to the stent-graft using a syringe pump by dispensing (4×1.3) µL onto the proximal end of the stent-graft as described above in the general procedure. The coated stent-graft was thereafter allowed to dry at room temperature overnight.

Example 1b: Coating of the Invention Containing Paclitaxel (100 µg Loading), Succinic Acid and Ethyl Urea—Stent-Graft 95 mg of paclitaxel, 12 mg of ethyl urea and 12 mg of succinic acid were added to a glass vial. A mixture of acetone (4 mL) and water (1 mL) was added to form a solution which was allowed to dissolve while stirring at room temperature. The resulting coating solution (19 mg paclitaxel/mL) was applied to the stent-graft using a syringe pump by dispensing (4×1.3) µL onto the proximal end of the stent-graft as described above in the general procedure. The coated stent-graft was thereafter allowed to dry at room temperature overnight.

Example 1c: Coating of the Invention Containing Paclitaxel (100 µg Loading), Glutaric Acid and Ethyl Urea—Stent-Graft 95 mg of paclitaxel, 12 mg of ethyl urea and 12 mg of glutaric acid were added to a glass vial. A mixture of acetone (4 mL) and water (1 mL) was added to form a solution which was allowed to dissolve while stirring at room temperature. The resulting coating solution (19 mg paclitaxel/mL) was applied to the stent-graft using a syringe pump by dispensing (4×1.3) µL onto the proximal end of the stent-graft as described above in the general procedure. The coated stent-graft was thereafter allowed to dry at room temperature overnight.

Example 1d: Comparator Coating Containing Paclitaxel (100 µg Loading) and Urea—Stent-graft 80 mg of paclitaxel and 20 mg of urea were added to a glass vial. A mixture of acetone (4 mL) and water (1 mL) was added to form a solution which was allowed to dissolve while stirring at room temperature. The resulting coating solution (16 mg paclitaxel/mL) was applied to the stent-graft using a syringe pump by dispensing (4×1.6) µL onto the proximal end of the stent-graft as described above in the general procedure. The coated stent-graft was thereafter allowed to dry at room temperature overnight.

Example 2: Analysis of the Paclitaxel Content of the Coated Stent-Grafts

In order to verify the actual amount of paclitaxel applied to the stent-grafts coated according to Examples 1a-1d, the amount of paclitaxel in the coating was determined using Test Method B-II. The amount of paclitaxel on the stent-grafts was 84.3±4.7, 84.8±9.3, 74.1±8.9 and 71 µg for Examples 1a, 1b, 1c and 1d respectively. The error is reported as the difference between each of the two data points and the mean for Examples 1a, 1b and 1c. The mean results are shown in Table 2.

TABLE 2

Paclitaxel content on stent grafts evaluated using Test Method B-II

| Example | Theoretical loading [µg] | Mean Ptx* content [µg] | N |
|---|---|---|---|
| 1a | 100 | 84 | 2 |
| 1b | 100 | 85 | 2 |
| 1c | 100 | 74 | 2 |
| 1d | 100 | 71 | 1 |

*Mean determined using Test Method B-II.

A minimal difference in paclitaxel loading on the stent-grafts of the different examples could be observed. A small variation of paclitaxel deposited on the stent-grafts is attributed to the application method and is not considered to be dependent on coating formulation.

Example 3: Analysis of the Paclitaxel Uptake in Porcine Tissue (In Vitro) of the Coated Stent-Grafts Stent-grafts prepared according to Examples 1a-d were examined for their ability to transfer paclitaxel from their surface to vascular tissue using Test Method A-II. Each coating was evaluated twice (N=2) apart from stent-grafts coated according to Example 1b which were also used as an internal reference for each evaluation of the stent-grafts for Examples 1a, 1c and 1d (hence N=8). The amount of paclitaxel in porcine tissue was 143.5±7.5, 112.7±38.8 145.0±43.0 and 57.0±1.9 µg/g tissue for Examples 1a, 1b, 1c and 1d respectively. The error is reported as the difference between each of the two data points and the mean for Examples 1a, 1c and 1d. The error for Example 1b is reported as standard deviation. The mean results can be seen in Table 3 and the "Mean normalized to coating 1b [%]" data is summarized in FIG. 1.

TABLE 3

Uptake of paclitaxel (in vitro) for stent-grafts of the invention (1a-1c) and comparator (1d)

| Example | Excipient | Mean Ptx uptake [μg/g tissue]* | Mean normalized to coating 1b [%] | N |
|---|---|---|---|---|
| 1a | Ethyl urea + caffeine | 143 | 107 | 2 |
| 1b | Ethyl urea + succinic acid | 113 | 100 | 8 |
| 1c | Ethyl urea + glutaric acid | 145 | 109 | 2 |
| 1d | Urea | 57 | 61 | 2 |

*Mean determined using Test Method A-II, Test Method B-II and UPLC evaluation.

It is evident from the results in the "Ptx Uptake" column of Table 3 that stent-grafts of the invention 1a, 1b and 1c achieved therapeutically relevant levels of paclitaxel uptake in vascular tissue. The results were normalized with regards to the internal reference (stent-grafts coated according to Example 1b) and calculated as mean values normalized to coating 1b (100%), as shown in the "Mean normalized to coating 1b" column of Table 3. These results are illustrated in FIG. 1, where it is evident that stent-grafts of the invention 1a, 1b and 1c showed a higher paclitaxel uptake in tissue than the stent-graft comparator 1d, using stent-graft 1b as an internal reference.

Example 4: Analysis of the Paclitaxel Content of the Coated Stent-Grafts Post Test Method A Stent-grafts previously examined for their ability to transfer paclitaxel from their surface to vascular tissue using Test Method A (i.e. the stent-grafts of Example 3) were analyzed to determine the amount of paclitaxel remaining on the device, using Test method B-II. The amount of paclitaxel on the stent-grafts was 49.5±7.0, 53.1±5.0, 50.0±4.9 and 42.4±7.8 μg for Examples 1a, 1b, 1c and 1d respectively. The error is reported as the difference between each of the two data points and the mean. The results are shown in Table 4.

TABLE 4

Post Test Method A paclitaxel content on stent grafts evaluated using Test Method B-II.

| Example | Excipient | Ptx content [μg] | Percent of theoretical loading 100 μg [%] | N |
|---|---|---|---|---|
| 1a | Ethyl urea + caffeine | 50 | 50 | 2 |
| 1b | Ethyl urea + succinic acid | 53 | 53 | 2 |
| 1c | Ethyl urea + glutaric acid | 50 | 50 | 2 |
| 1d | Urea | 42 | 42 | 2 |

It was found that the paclitaxel content on stent-grafts of the invention (1a, 1b and 1c) was higher post Test Method A was higher compared to the comparator stent-graft id. When these results are taken together with the data of Table 3 in Example 3 (uptake of paclitaxel), it is interesting to note that stent-grafts of the invention exhibited higher paclitaxel uptake into the vascular tissue, and also higher paclitaxel content remaining on the spent device, compared with the comparator 1d which exhibited lower paclitaxel update, and also lower paclitaxel content remaining on the spent device. This indicates a higher efficiency in terms of uptake of paclitaxel in tissue for devices of the invention 1a, 1b and 1c when compared to the comparator 1d.

Example 5—Construction of an ePTFE Covered Balloon for Use with the Coating of the Invention Expanded polytetrafluoroethylene (ePTFE) material was obtained with the following typical properties: thickness of 38.1 microns, width of 2.7 cm, mass/Area of 8.73 g/m$^2$, longitudinal (i.e., "machine direction") matrix tensile strength (MTS) of 283.5 MPa, transverse MTS of 11.0 MPa, longitudinal force to break of 0.112 kgf/mm, and IPA bubble point of 9.93 kPa.

A 1.7 mm×170 mm stainless steel mandrel was obtained and a length of the ePTFE material described above was cut to 160 mm. The ePTFE piece was wrapped longitudinally around the mandrel (i.e., "cigarette-wrapped") approximately five times, with the machine direction parallel to the length of the mandrel.

Another type of ePTFE material was obtained to serve as a manufacturing aid. This ePTFE had the following typical properties: thickness of 8.9 microns, width of 24 mm, mass/Area of 2.43 g/m$^2$, longitudinal MTS of 661.9 MPa, transverse MTS of 9.9 MPa, and IPA bubble point of 4.83 kPa.

This second ePTFE material was helically wrapped over the first ePTFE wrapped tube on a first bias at a 45 degree pitch with a 50% overlap from one end of the previously wrapped tube to the other and then on a reversed bias at a 45 degree pitch from end to end of the underlying wrapped ePTFE tube. This produced approximately 4 layers of overwrap.

The mandrel and ePTFE wraps were thermally treated for 3 minutes at 380° C. and allowed to cool to room temperature. The helical ePTFE overwrap was removed and discarded.

A nylon tube was obtained having an inside diameter of 2.16 mm and a 0.038 mm wall thickness. The first ePTFE material wrapped tube was trimmed to a length of 44 mm on the mandrel and removed from the mandrel. The inside diameter of the ePTFE tube was increased to fit over the nylon tube by using a tapered stainless steel mandrel. The ePTFE tube was then positioned co-radially over the nylon tube.

A 5 mm×40 mm long nylon balloon catheter with a 0.89 mm guidewire lumen was obtained (Bavaria Medizin Technologie, model # BMT-035, article #08GL-504A). A 0.89 mm stainless steel mandrel was inserted into the distal guidewire lumen of the balloon catheter to stiffen the area of the catheter proximate the balloon. The balloon was inflated to 2 atmospheres. The partially inflated balloon was manually dipped into a solution comprising Fluorinert FC-72 (3M, Saint Paul, Minn.) and a thermoplastic fluoroelastomer copolymer of tetrafluoroethylene/perfluoromethylvinylether (TFE/PMVE) as taught in U.S. Pat. Nos. 7,049,380 and 8,048,440 (Gore Enterprise Holdings, Inc., incorporated herein by reference).

The balloon was held in the solution for approximately 1 second, removed and gently tapped to remove excess of the solution. The coated balloon was allowed to dry for 15 seconds. This manual dip coating process was repeated 3 times to produce 3 coats over the balloon. The balloon was then deflated to approximately its original compacted diameter by pulling a vacuum on its catheter inflation port.

The nylon tube and ePTFE wrapped tube assembly as described above was fitted co-radially over the re-compacted and coated balloon and centered on the balloon catheter radiopaque marker bands. The ePTFE wrapped tube was held in place while the nylon tube was manually removed. The balloon was inflated to approximately 2-3 atmospheres for 30 seconds. This created an adhesive bond between the inner wall of the ePTFE wrapped tube and the TFE/PMVE coating on the nylon balloon. The balloon was then deflated to approximately its original compacted dimensions.

Example 6: Method for Preparing Coating of the Invention—Balloons

Two types of balloons, one comprising nylon and the other comprising ePTFE were utilized. The balloons were over-coated using the following general procedure.

Coating formulations of the invention containing paclitaxel, ethyl urea and caffeine; paclitaxel, ethyl urea and succinic acid; and paclitaxel, ethyl urea and glutaric acid were prepared by dissolving the paclitaxel, ethyl urea and caffeine or succinic acid or glutaric acid, as appropriate, in acetone/water (80/20 (v/v)). The balloons (5 mm diameter) were coated while inflated (covering the whole device, 40 mm) by dispensing the coating solution (using a pipette while moving rotating the balloon manually).

The components of each formulation are shown in Table 5 and specific methods described in Examples 6a, 6b and 6c below.

As a comparative example, a coating solution containing paclitaxel and urea was prepared as described in Example 6d.

The final paclitaxel loading on the coated area for nylon balloons was approximately 4.0 µg/mm$^2$.

The final paclitaxel loading on the coated area for ePTFE balloons was approximately 3.2 µg/mm$^2$.

TABLE 5

Coating formulations for preparing balloons of the invention (6a-6c) and comparator (6d)

| Example | Ptx [mg] | Ethyl urea [mg] | Caffeine [mg] | Succinic acid [mg] | Glutaric acid [mg] | Urea [mg] | Acetone [mL] | Water [mL] |
|---|---|---|---|---|---|---|---|---|
| 6a | 95 | 12 | 12 | — | — | — | 4 | 1 |
| 6b | 95 | 12 | — | 12 | — | — | 4 | 1 |
| 6c | 95 | 12 | — | — | 12 | — | 4 | 1 |
| 6d | 80 | — | — | — | — | 20 | 4 | 1 |

Example 6a: Coating of the Invention Containing Paclitaxel (2.0 or 2.5 mg Loading), Caffeine and Ethyl Urea—Balloon 95 mg of paclitaxel, 12 mg of ethyl urea and 12 mg of caffeine were added to a glass vial. A mixture of acetone (4 mL) and water (1 mL) was added to form a solution which was allowed to dissolve while stirring at room temperature. The resulting coating solution (19 mg paclitaxel/mL) was applied to the balloon using a pipette by dispensing 105 or 131 µL (according to desired loading) onto the balloon as described above in the general procedure. The coated balloon was thereafter allowed to dry at room temperature overnight.

Example 6b: Coating of the Invention Containing Paclitaxel (2.0 or 2.5 mg Loading), Succinic Acid and Ethyl Urea—Balloon 95 mg of paclitaxel, 12 mg of ethyl urea and 12 mg of succinic acid were added to a glass vial. A mixture of acetone (4 mL) and water (1 mL) was added to form a solution which was allowed to dissolve while stirring at room temperature. The resulting coating solution (19 mg paclitaxel/mL) was applied to the stent-graft using a pipette by dispensing 105 or 131 µL (according to desired loading) onto the balloon as described above in the general procedure. The coated balloon was thereafter allowed to dry at room temperature overnight.

Example 6c: Coating of the Invention Containing Paclitaxel (2.0 or 2.5 mg Loading), Glutaric Acid and Ethyl Urea—Balloon 95 mg of paclitaxel, 12 mg of ethyl urea and 12 mg of glutaric acid were added to a glass vial. A mixture of acetone (4 mL) and water (1 mL) was added to form a solution which was allowed to dissolve while stirring at room temperature. The resulting coating solution (19 mg paclitaxel/mL) was applied to the balloon using a pipette by dispensing 105 or 131 µL (according to desired loading) onto the balloon as described above in the general procedure. The coated balloon was thereafter allowed to dry at room temperature overnight.

Example 6d: Comparator Coating Containing Paclitaxel (2.5 mg Loading) and Urea—Balloon 80 mg of paclitaxel and 20 mg of urea were added to a glass vial. A mixture of acetone (4 mL) and water (1 mL) was added to form a solution which was allowed to dissolve while stirring at room temperature. The resulting coating solution (16 mg paclitaxel/mL) was applied to the balloon using a pipette by dispensing 156 µL onto the balloon as described above in the general procedure. The coated balloon was thereafter allowed to dry at room temperature overnight.

Example 7: Analysis of the Paclitaxel Content of the Coated Balloons

In order to verify the actual amount of paclitaxel applied to the balloons coated according to Examples 6a-6d, the amount of paclitaxel in the coating was determined using Test Method B-II. The found Ptx content ranged from 2.2-2.4 mg for the nylon balloon and 1.9-2.2 mg for the ePTFE balloon. The results are shown in Table 5. A commercially available balloon marketed by Medtronic sold under the brand name IN.PACT Admiral Drug-Coated Balloon was also evaluated. The theoretical loading is unknown but the measured valued was 2.46±0.05 µg. The error is reported as the difference between each of the two data points and the mean.

TABLE 6

Paclitaxel content on balloons evaluated using Test Method B-II

| Example | Balloon type | Theoretical loading [mg] | Ptx content [mg] | N |
|---|---|---|---|---|
| 6a | Nylon | 2.5 | 2.2 | 1 |
| 6b | Nylon | 2.5 | 2.3 | 1 |
| 6c | Nylon | 2.5 | 2.2 | 1 |
| 6d | Nylon | 2.5 | 2.4 | 1 |
| 6a | ePTFE | 2.0 | 2.2 | 1 |
| 6b | ePTFE | 2.0 | 1.9 | 1 |

TABLE 6-continued

Paclitaxel content on balloons evaluated using Test Method B-II

| Example | Balloon type | Theoretical loading [mg] | Ptx content [mg] | N |
|---|---|---|---|---|
| 6c | ePTFE | 2.0 | 2.0 | 1 |
| — | Commercial balloon | N/A | 2.5 | 2 |

The results from Table 6 indicate that the coating formulations of Example 6a-6c may be applied to a variety of materials.

Example 8: Analysis of the Paclitaxel Update in Porcine Tissue (In Vitro) of the Coated Balloons Nylon Balloons Nylon balloons prepared according to Examples 6a to 6d were examined in vitro for their ability to transfer paclitaxel from their surface to vascular tissue using according to Test Method A-I. Each coating was evaluated twice (N=2) apart from balloons coated according to Example 6b which were also used as an internal reference for each evaluation of the stent-grafts for Examples 6a, 6c and 6d (hence N=8). The amount of paclitaxel found in porcine tissue was 201±67, 343±140, 389±225 and 282±36 µg/g tissue for Examples 6a, 6b, 6c and 6d respectively. The error is reported as the difference between each of the two data points and the mean for Examples 6a, 6c and 6d. The error for Example 6b is reported as standard deviation. The results can be seen in Table 7 and the "Mean normalized to coating 6b [%]" data is summarized in FIG. 2.

TABLE 7

Uptake of paclitaxel (in vitro) for nylon balloons of the invention (6a-6c) and comparator (6d)

| Example | Balloon type | Excipient | Mean Ptx uptake [µg/g tissue] | Mean normalized to coating 6b [%] | N |
|---|---|---|---|---|---|
| 6a | Nylon | Ethylurea + caffeine | 201 | 116 | 2 |
| 6b | Nylon | Ethylurea + succinic acid | 343 | 100 | 8 |
| 6c | Nylon | Ethylurea + glutaric acid | 389 | 204 | 2 |
| 6d | Nylon | Urea | 282 | 61 | 2 |

Figure 2:
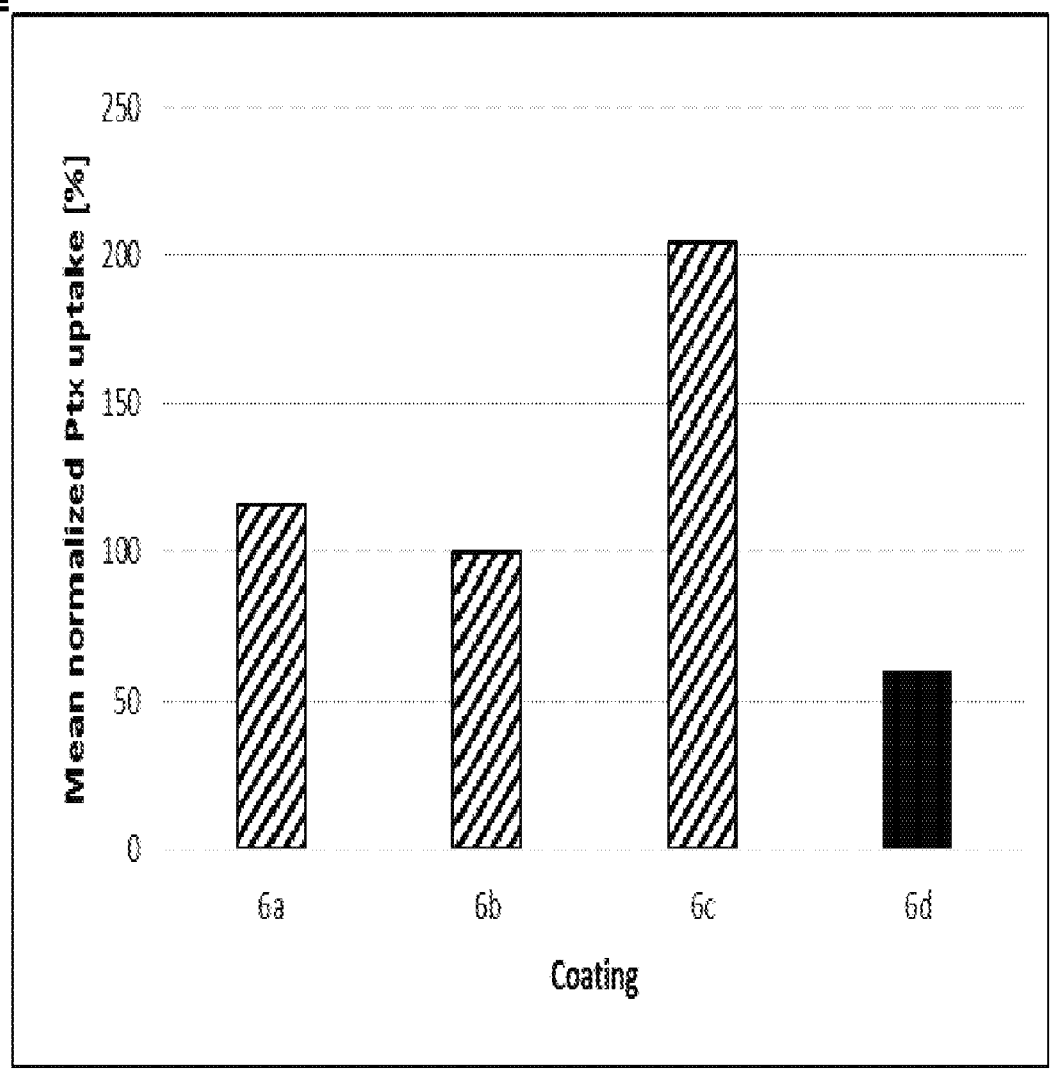
FIG. 2 shows the normalized percent uptake of paclitaxel (in vitro) in porcine tissue for coated balloons of the invention compared with a comparator (Example 8).

It is evident from the results in the "Ptx Uptake" column of Table 7 that nylon balloons of the invention 6a, 6b and 6c achieved therapeutically relevant levels of paclitaxel uptake in vascular tissue. The results were normalized with regards to the internal reference (balloons coated according to Example 6b) and calculated as mean values normalized to coating 6b (100%), as shown in the "Mean normalized to coating 6b" column of Table 7. These results are illustrated in FIG. 2, where it is evident that nylon balloons of the invention 6a, 6b and 6c showed a higher paclitaxel update in tissue than the nylon balloon comparator 6d, using balloon 6b as an internal reference.

ePTFE Balloons ePTFE balloons prepared according to Examples 6a to 6d were examined for their ability to transfer paclitaxel from their surface to vascular tissue using according to Test Method A-I. Each coating was evaluated twice (N=3). The amount of paclitaxel found in porcine tissue was 377±110, 211±66 and 242±76 µg/g tissue for Examples 6a, 6b and 6c respectively. The error is reported as standard deviation. The mean results can be seen in Table 8.

TABLE 8

Uptake of paclitaxel for ePTFE balloons of the invention (6a-6c).

| Example | Balloon type | Excipient | Ptx uptake [µg/g tissue] | Percentage of coating 3b [%] | N |
|---|---|---|---|---|---|
| 6a | ePTFE | Ethylurea + caffeine | 377 | 179 | 3 |
| 6b | ePTFE | Ethylurea + succinic acid | 211 | 100 | 3 |
| 6c | ePTFE | Ethylurea + glutaric acid | 242 | 115 | 3 |

As can be seen from Table 8, the paclitaxel can migrate from the implantable device into the vessel wall in therapeutically relevant levels for coated ePTFE balloons 6a-6c.

Example 9: Analysis of the Paclitaxel Content of the Coated Balloons Post Test Method A Nylon and ePTFE ballons previously examined for their ability to transfer paclitaxel from their surface to vascular tissue using Test Method A (i.e. the balloons of Example 8) were analyzed to determine the amount of paclitaxel remaining on the device, using Test Method B-II.

For nylon balloons, the amounts of paclitaxel found was 355.7±139.7, 437.2±177.9, 558.5±24.2 and 525.4±37.5 µg for Examples 6a, 6b, 6c and 6d respectively. The error is reported as the difference between each of the two data points and the mean for Examples 6a, 6c and 6d. The error for Example 6b is reported as standard deviation. The mean results are shown in Table 9.

For ePTFE balloons, the amount of paclitaxel found was 1000±91.1, 1011±55.1 and 1167±79.9 µg for Example 6a, 6b and 6c respectively. The error is reported as standard deviation. The mean results are shown in Table 9.

TABLE 9

Post Method A paclitaxel content on balloons evaluated using Test Method B-II

| Example | Ballon type | Excipient | Ptx content [µg/g tissue] | Percent remaining of initial loading 2500 µg [%]*** | N |
|---|---|---|---|---|---|
| 6a | Nylon | Ethyl urea/caffeine | 356 | 14 | 2 |
| 6b | Nylon | Ethyl urea/succinic acid | 437 | 17 | 8 |
| 6c | Nylon | Ethyl urea/glutaric acid | 559 | 22 | 2 |
| 6d | Nylon | Ethyl urea | 525 | 21 | 2 |
| 6a | ePTFE | Ethyl urea/caffeine | 1000 | 75 | 3 |
| 6b | ePTFE | Ethyl urea/succinic acid | 1011 | 40 | 3 |
| 6c | ePTFE | Ethyl urea/glutaric acid | 1167 | 47 | 3 |

*Error reported as the difference between each of the two data points and the mean
**Error reported as standard deviation It can be seen from the data in Table 9 that the three coated ePTFE balloons (6a-6c, ePTFE) retained greater levels of paclitaxel following the in vitro analysis of Test A, compared to the nylon balloons.

Example 10: 1 Day Analysis of Paclitaxel Uptake in Porcine Tissue (In Vivo) of the Coated Balloons Coated ePTFE balloons prepared according to Examples 6a-6c were sterilized using ethylene oxide according to Test Method E and then examined for their ability to transfer paclitaxel from their surface to vascular tissue in vivo using Test Method D. The tissue in the treatment zone of the vessel was collected after one (1) day and evaluated for paclitaxel content using UPLC (as described in the Evaluation Methods). As a comparative example, a commercially available balloon marketed by Medtronic/Invatec sold under the name IN.PACT Admiral Drug-Coated Balloon marketed as "paclitaxel-eluting" with a coating containing paclitaxel and urea was also tested. The amount of paclitaxel found in tissue from the in vivo test was 195.5±127.0, 170.3±204.2 and 171.7±127.6 µg/g tissue for Examples 6a, 6b and 6c respectively. The amount of paclitaxel found in tissue was 29.9±32.2 µg/g for the IN.PACT Admiral balloon. The error is reported as standard deviation. The mean results are shown in Table 10 and the paclitaxel uptake ("Ptx Uptake") data is summarized in FIG. 3.

The amount of paclitaxel found on balloons post the in vivo test was 42.4±1.6, 44.3±3.3 and 42.6±4.5 µg for Examples 6a, 6b and 6c respectively. The error is reported as standard deviation. The mean results are shown in Table 10.

TABLE 10

1 day uptake of paclitaxel (in vivo) for ePTFE balloons of the invention (6a-6c) and comparator

| Example | Excipient | Mean Ptx uptake [µg/g tissue] | Ptx dose [µg/mm$^2$] | Remaining mean Ptx on sample post treatment [%] | N |
| --- | --- | --- | --- | --- | --- |
| 6a | Ethyl urea + caffeine | 196 | 3.2* | 42 | 3 |
| 6b | Ethyl urea + succinic acid | 170 | 3.2* | 44 | 3 |
| 6c | Ethyl urea + glutaric acid | 172 | 3.2* | 43 | 3 |
| — | Urea$^a$ | 30 | 3.5 | N/T | 8 |

Figure 3:
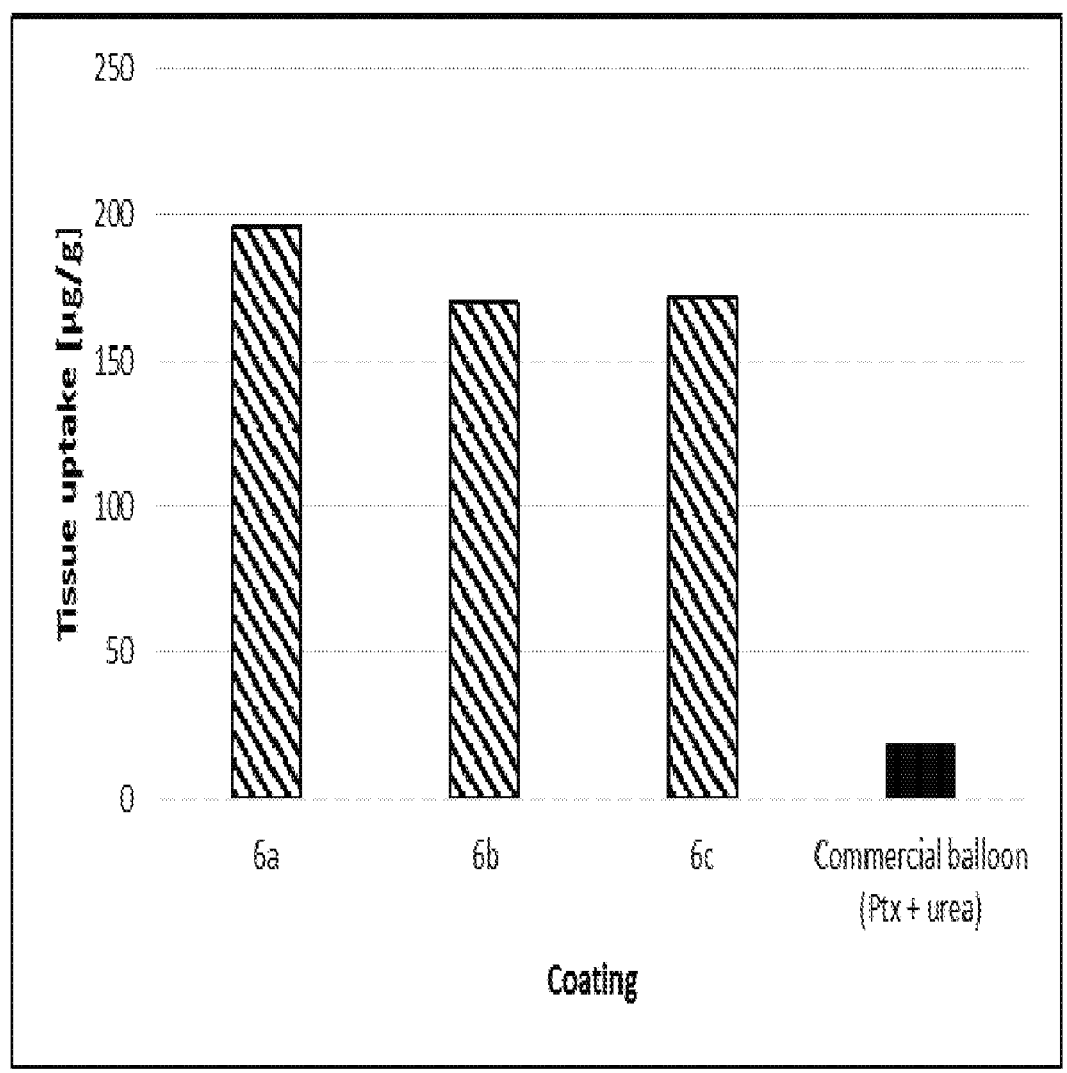
FIG. 3 shows paclitaxel uptake (in vivo) in porcine tissue after 1 day for coated balloons of the invention compared with a commercially available paclitaxel-containing balloon as comparator (Example 10).

$^a$Commercially available balloon with a coating containing paclitaxel and urea
*Based on theoretical loading of 2.0 mg/balloon It can be seen from Table 10 and FIG. 3 that the commercially available balloon with a coating containing paclitaxel and urea resulted in a lower uptake of paclitaxel after 1 day, compared with the coated balloons of the invention (6a-6c).

Example 11: 29 Day Analysis of Paclitaxel Uptake in Porcine Tissue (In Vivo) of the Coated Balloons Coated ePTFE balloons prepared according to Examples 6a-6c were sterilized by ethylene oxide according to Test Method E and then examined for their ability to transfer paclitaxel from their surface to vascular tissue in vivo using Test Method D. The tissue in the treatment zone of the vessel was collected after twenty-nine (29) days and evaluated for paclitaxel content using UPLC (as described in the Evaluation Methods) analysis. The amount of paclitaxel found in tissue from the in vivo test was 3.6±1.8, 2.3±2.1 and 2.9±1.7 µg/g tissue for Examples 6a, 6b and 6c respectively. The error is reported as the difference between each of the two data points and the mean. The mean results are shown in Table 11 and the paclitaxel uptake ("Ptx uptake") data is summarized in FIG. 4.

TABLE 11

29 day uptake of paclitaxel (in vivo) for ePTFE balloons of the invention

| Example | Excipient | Ptx uptake [µg/g tissue] | Ptx dose [µg/mm$^2$]* | N |
| --- | --- | --- | --- | --- |
| 6a | Ethyl urea + caffeine | 3.6 | 3.2 | 2 |
| 6b | Ethyl urea + succinic acid | 2.3 | 3.2 | 2 |
| 6c | Ethyl urea + glutaric acid | 2.9 | 3.2 | 2 |

*Based on theoretical loading of 2.0 mg/balloon

Figure 4:
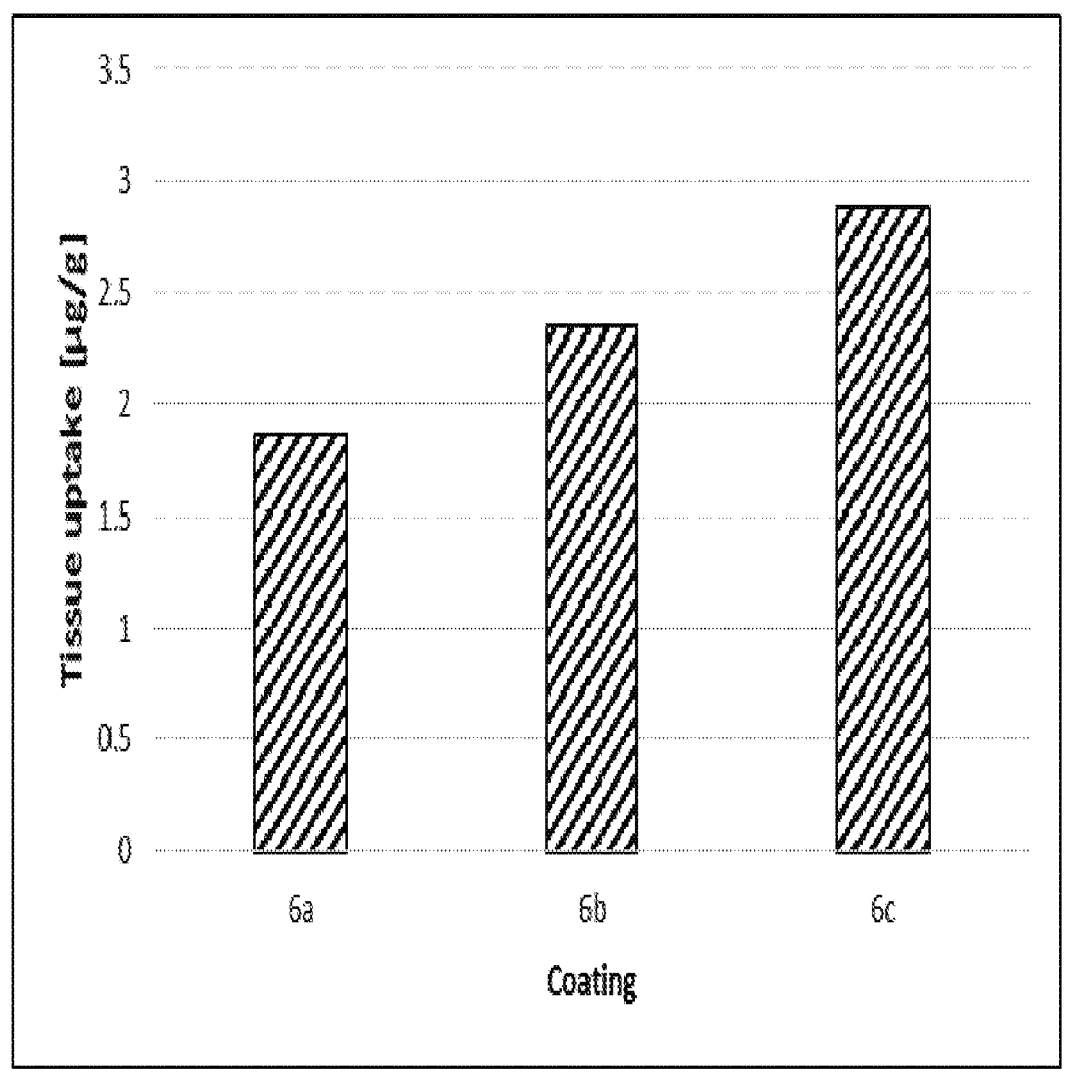
FIG. 4 shows paclitaxel uptake (in vivo) in porcine tissue after 29 days for coated balloons of the invention (Example 11).

It is evident from Table 11 and FIG. 4 that balloons of the invention 6a-6c delivered therapeutically relevant levels of paclitaxel over a 29 day period.

Example 12: Adhesion Test Analysis of Coating of Balloons Prepared According to Example 6

The adhesion of the coating layer of the balloons prepared according to Example 6a-6d was investigated. Adhesion was assessed by comparing the content of paclitaxel on the balloon (according to Test Method B-II) before and after a shake test (according to Test Method Q). For nylon balloons, the amount of paclitaxel lost was 441±300, 287±259 and 68.9±13.5 µg for Examples 6a, 6b, 6c and 6d respectively. The error is reported as the difference between each of the two data points and the mean. The results are summarized in Table 12 and FIG. 5, where a lower percentage of paclitaxel lost indicates better adhesion and a more durable coating layer.

For ePTFE balloons, the amount of paclitaxel lost was 107.3±9.2, 121.2±23.7, 631±6 and 697±92 µg for Examples 6a, 6b and 6c respectively. The error is reported as standard deviation. The results are summarized in Table 12 and FIG. 5, where a lower percentage of paclitaxel lost indicates better adhesion and a more durable coating layer.

TABLE 12

Paclitaxel content on balloons pre- and post- shake test

| Example | Balloon type | Theoretical Ptx loading [mg] | Mean Ptx lost in shake test [µg] | Mean Ptx loss [%] | N |
| --- | --- | --- | --- | --- | --- |
| 6a | Nylon | 2.5 | 441 | 20 | 2 |
| 6b | Nylon | 2.5 | 287 | 12 | 2 |
| 6c | Nylon | 2.5 | 631 | 28 | 2 |
| 6d | Nylon | 2.5 | 697 | 29 | 2 |
| 6a | ePTFE | 2.5 | 107 | 5 | 3 |
| 6b | ePTFE | 2.5 | 121 | 6 | 3 |
| 6c | ePTFE | 2.5 | 69 | 3 | 3 |

The results show that the coatings of balloons of the invention (6a-6c) generally exhibited better adherence compared with the comparator balloon 6d. Balloons of the invention composed of ePTFE exhibited better adherence compared with balloons composed of nylon.

Example 13: Analysis of Paclitaxel Degradation Products of Coated Balloons Post Sterilization Coated ePTFE balloons prepared according to Examples 6a, 6b and 6c were sterilized using ethylene oxide according to Test Method E, and then the coatings were analyzed for the presence of known degradation products of paclitaxel as described in the evaluation methods ("Degradation products of paclitaxel") using UPLC. The results are shown in Table 13.

TABLE 13

Determination of paclitaxel degradation products on coated balloon following sterilization

| Example | Excipient | % Related substances |
|---|---|---|
| 3a | Ethyl urea + caffeine | <1% |
| 3b | Ethyl urea + succinic acid | <1% |
| 3c | Ethyl urea + glutaric acid | <1% |

All coatings had less than 1% of the known paclitaxel degradation products post-sterilization, indicating that the paclitaxel formulated in the coating is stable to sterilization by ethylene oxide.

Example 14: Methods for Preparing an Immobilized Heparin Coating on a Medical Device In certain embodiments of the invention the medical device also has a coating of heparin, suitably immobilized heparin. The heparin layer is preferably applied the device prior to applying the coating layer comprising components i), ii) and iii). The following are non-limiting examples for preparing an immobilized coating of heparin.

The surface of the medical device to be coated is pre-treated (cleaned) with isopropanol and an oxidizing agent. The surface is then treated using the method described in Larm et al. in EP-B-0086186 and EP-B-495820 to form coating bilayers ending with a layer of sulfated polysaccharide.

The bilayers are built-up by alternating adsorption of a positively charged polyamine (polyethyleneimine (e.g. as used in the examples of EP0495820B1) and negatively charged sulfated polysaccharide (dextran sulfate). Polyethyleneimine is diluted with water to prepare a stock solution (5 g polyethyleneimine was added to 20 mL purified water). The polyamine is cross-linked with a di-functional aldehyde (crotonaldehyde). Every pair of polyamine and sulfated polysaccharide is called one bilayer. The surface of the device is primed with four bilayers, the final layer being dependent on the subsequent method of immobilizing the heparin moiety.

Immobilization of heparin as described in EP-B-0086186—via reductive amination. Heparin is subjected to degradation by diazotation to form terminal (end point) free aldehyde group, which subsequently reacts via the aldehyde with an amino group on the surface of the implantable medical device to form a Schiff base which is converted to a secondary amine linker by reduction.

A solution of heparin (1 g) in 300 ml water is cooled to 0° C. on an ice bath. Sodium nitrite (10 mg) is added with stirring. Then acetic acid is added drop-wise (2 ml). The solution is allowed to stand under stirring for two more hours at 0° C. The reaction mixture is worked up by dialysis against distilled water and lyophilization to produce end-point aldehyde-functionalized heparin.

The surface of the device to be heparinized is primed with four bilayers as described above, ending with a final layer of polyethyleneimine (e.g. as used in the examples of EP0495820B1). Following rinsing, the surface to be coated is incubated with a solution of the end-point aldehyde-functionalized heparin (2-20 mg/mL) and sodium cyanoborohydride (0.5 mg/ml) in a phosphate buffer at pH 7.0 for 24 hours at room temperature. The heparinized surface is carefully rinsed with water.

Immobilization as described in WO2011/110684—via a thioether linker. Thiol-functionalized heparin is reacted with a maleimide-functionalized polyamine surface Thiol-functionalized heparin is prepared as follows. Nitrite-degraded heparin with end-point aldehyde groups (prepared as described above) (5.00 g, 1.0 mmol), cysteamine hydrochloride (0.57 g, 5.0 mmol) and sodium chloride (0.6 g) are dissolved in purified water. The pH is adjusted to 6.0 with 1 M NaOH (aq) and 1 M HCl (aq). To the solution is added 3.1 ml of 5% (aq.) $NaCNBH_3$ (0.16 g, 2.5 mmol) and the reaction is stirred overnight at room temperature. The pH is adjusted to 11.0 with 1 M NaOH (aq) and the resulting product is dialyzed against purified water with a SpectraPor dialysis membrane mwco 1 kD (flat width 45 mm) for three days.

The reaction mixture is then concentrated and freeze dried to obtain 2.6 g of the thiol-functionalized heparin (at the C1 of the reducing terminal) as a white fluffy powder.

Maleimide-functionalized polyethyleneimine (polyethyleneimine as used in the examples of EP0495820B1 (above)) is prepared as follows. 4-maleimidobutyric acid (0.50 g, 2.7 mmol) and N-hydroxysuccinimide (NHS) (0.32 g, 2.7 mmol) are dissolved in 3 mL of dichloromethane and stirred at 0° C. A solution of N,N'-dicyclohexylcarbodiimide (0.56 g, 2.7 mmol) in 3 mL of dichloromethane is added slowly to the reaction mixture at 0° C. The reaction mixture is stirred overnight and the byproducts are filtered off and the NHS activated 4-maleimidobutyric acid is concentrated and dried under vacuum. The dried NHS activated 4-maleimidobutyric acid is dissolved in 30 mL of purified water and mixed with 7.6 mL of the polyethyleneimine stock solution at 0° C. and left to react overnight at room temperature to obtain a 1% solution of the maleimide functionalized polyethyleneimine.

The surface of the device to be heparinized is primed with four bilayers as described above, ending with a final layer of negatively charged sulfated polysaccharide (dextran sulfate). Then next coating step uses a solution of 10 mL of a 1% solution of the maleimide-functionalized polyethyleneimine in 1000 mL of a 0.04 M/0.04 M borate/phosphate buffer at pH 8.0. The adsorption of the maleimide-functionalized polyethyleneimine to the sulfate surface is carried out for 20 minutes at room temperature. A two minute water rinse is performed after the adsorption to rinse off excess polymer. 500 mg of thiol functionalized heparin is dissolved in 1000 mL of de-ionized water and 50 mg tris(2-carboxyethyl)phosphine hydrochloride, 500 mg 4,4'-azobis(4-cyanovaleric acid), and 2.9 g NaCl were added. The pH is adjusted to 3.7 with 1 M HCl (aq).

The reaction between the solution of the thiol-functionalized heparin and the maleimide functionalized polyethyleneimine surface is carried out at 70° C. for 3 h. Purification is performed by rinsing off non-covalently linked heparin for 10 minutes using a 0.04 M/0.04 M borate/phosphate buffer at pH 8.0. A final rinse with de-ionized water for two minutes is performed to wash away buffer salt residues. The flow used during the entire process is 100 mL/min.

Example 15: Stent-Grafts of the Invention Also Including an Immobilized Heparin Coating Layer—Analysis of Heparin Bioactivity As discussed in Example 1, coated stent-grafts prepared according to Example 1 utilized a stent-graft device which had been purchased with a pre-coating layer of immobilized heparin. Following coating with paclitaxel, ethyl urea and caffeine or succinic acid or glutaric acid (as described in Examples 1a, 1b and 1c) the devices were manipulated and the paclitaxel coating layer extracted according to Test Method B-III. The heparin bioactivity of the resulting device (bearing an immobilized heparin coating) was assessed according to Test Method M. All devices 1a, 1b and 1c were found to have heparin bioactivity values of >1 pmol/cm$^2$ which corresponds to a therapeutically relevant level.

The invention claimed is:

1. A medical device for delivering a therapeutic agent to a tissue, the device having a coating layer applied to a surface of the device, the coating layer consisting of components i), ii) and iii), wherein
   component i) is a therapeutic agent which is paclitaxel; and
   component ii) is ethyl urea or a pharmaceutically acceptable salt thereof; and
   component iii) is succinic acid, glutaric acid, or a pharmaceutically acceptable salt of either one thereof.

2. A medical device according to claim 1, wherein the coating layer consists of a mixture of components i), ii) and iii).

3. A medical device according to claim 1, wherein the proportion of component i) in the coating layer is 10-95% by weight; and/or wherein the proportion of component ii) in the coating layer is 1-95% by weight; and/or
   wherein the proportion of component iii) in the coating layer is 1-95% by weight.

4. A medical device according to claim 1, wherein the coating layer is formed by evaporation of one or more solutions comprising component i) and/or component ii) and/or component iii).

5. A medical device according to claim 4, wherein the one or more solutions are independently solutions in a solvent selected from water, acetone, alcohols (such as methanol, ethanol, propanol and isopropanol), tetrahydrofuran, DMF, DMSO, EtOAc, dioxane and mixtures thereof.

6. A medical device according to claim 1, wherein at least a portion of a surface of the device being coated is porous.

7. A medical device according to claim 1, which is a balloon catheter, a stent, a stent-graft or a graft.

8. A medical device according to claim 1, which coating layer consisting of components i), ii) and iii) has suitable adherence such that less than 40% of component i) is lost during shaking using Test Method Q; and/or
   which device has paclitaxel release and tissue transfer characteristics such that using Test Method A-I or A-II as appropriate, the measured paclitaxel concentration in the tissue at the given time point is at least 1 µg drug per g tissue (µg/g).

9. A medical device according to claim 1, wherein component i) when formulated in the coating layer, is stable to ethylene oxide
   sterilization such that at least 80% by weight of component i) is retained following sterilization using Test Method E.

10. A method for the prevention or treatment of stenosis or restenosis which comprises inserting transiently or permanently into a blood vessel in the human body a medical device according to claim 1.

11. A composition consisting of a mixture of components i), ii) and iii), wherein:
   component i) is paclitaxel; and
   component ii) is ethyl urea or a pharmaceutically acceptable salt thereof; and
   component iii) succinic acid, glutaric acid or a pharmaceutically acceptable salt of either one thereof.

12. A composition according to claim 11, in the farm of a coating applied to a surface.

13. A composition according to claim 11, wherein the proportion of component i) in the mixture of components i), ii) and iii) 10-95% weight; and/or
   wherein the proportion of component ii) in the mixture of components i), ii) and iii) is 1-95% by weight; and/or
   wherein the proportion of component iii) in the mixture of components i), ii) and iii) is 1-95% by weight.

14. A composition according to claim 11, wherein the coating layer is formed by evaporation of a solution of the components i), ii) and iii).

15. A medical device according to claim 1 which has been ethylene oxide sterilized.

16. A process for preparing a coating layer on a surface of a medical device which consists of the steps of:
   a) dissolving components i), ii) and iii) in one or more solvents to form one or more solutions, wherein
   component i) is a therapeutic agent which is paclitaxel; and
   component ii) is ethyl urea or a pharmaceutically acceptable salt thereof; and
   component iii) is succinic acid or glutaric acid; and
   b) coating a surface of the device with each of the said one or more solutions of step a); and
   c) evaporating the solvent; or
   a process for preparing a coating layer on a surface of a medical device which consists of the steps of:
   a) dissolving components i), ii) and iii) in a solvent to form a solution, wherein component i) is a therapeutic agent which is paclitaxel; and
   component ii) is ethyl urea or a pharmaceutically acceptable salt thereof; and
   component iii) is succinic acid or glutaric acid or a pharmaceutically acceptable salt of either one thereof; and
   b) coating a surface of the device with the solution of step a); and
   c) evaporating the solvent.

17. The medical device according to claim 1, wherein the coating layer is surfactant-free.

* * * * *